United States Patent
Rakshit

(10) Patent No.: US 11,860,584 B2
(45) Date of Patent: Jan. 2, 2024

(54) DYNAMICALLY CONTROLLABLE SMARTWATCH

(71) Applicant: INTERNATIONAL BUSINESS MACHINES CORPORATION, Armonk, NY (US)

(72) Inventor: Sarbajit K. Rakshit, Kolkata (IN)

(73) Assignee: International Business Machines Corporation, Armonk, NY (US)

( * ) Notice: Subject to any disclaimer, the term of this patent is extended or adjusted under 35 U.S.C. 154(b) by 556 days.

(21) Appl. No.: 16/895,753

(22) Filed: Jun. 8, 2020

(65) Prior Publication Data
US 2021/0382441 A1    Dec. 9, 2021

(51) Int. Cl.
| | | |
|---|---|---|
| G04G 17/04 | (2006.01) | |
| G04G 21/02 | (2010.01) | |
| G06N 20/00 | (2019.01) | |
| G16H 40/63 | (2018.01) | |
| G06F 40/20 | (2020.01) | |

(52) U.S. Cl.
CPC ......... *G04G 17/045* (2013.01); *G04G 21/025* (2013.01); *G06N 20/00* (2019.01); *G16H 40/63* (2018.01); *G06F 40/20* (2020.01)

(58) Field of Classification Search
CPC .... G04G 17/045; G04G 21/025; G04G 9/007; G06N 20/00; G16H 40/63; G16H 20/30; G16H 50/30; G06F 40/20; G06F 40/284; G06F 40/30
See application file for complete search history.

(56) References Cited

U.S. PATENT DOCUMENTS

| | | | |
|---|---|---|---|
| 10,224,035 B1 * | 3/2019 | Koenig | ................... G10L 15/22 |
| 2017/0164878 A1 | 6/2017 | Connor | |
| 2018/0137801 A1 * | 5/2018 | An | ......................... G06T 3/0093 |
| 2019/0043845 A1 | 2/2019 | Bibl et al. | |
| 2019/0069842 A1 | 3/2019 | Rothberg et al. | |

FOREIGN PATENT DOCUMENTS

| | | | |
|---|---|---|---|
| DE | 102015104767 B4 | 10/2019 | |
| KR | 20180026620 A * | 9/2016 | ............. G04G 21/02 |

OTHER PUBLICATIONS

Anonymous, "Dynamically locating display area on full screen bracelet", IP.com No. IPCOM000248853D, Jan. 18, 2017, 7 pgs.
Kim, M., "Wearables still haven't solved the problems of skin science, but new ideas are coming", Health and Wellbeing Wearable Technology Feature, Nov. 18, 2017 (retrieved from Internet URL: https://www.wareable.com/health-and-wellbeing/skin-science-complex-wearables-4441 on Feb. 13, 2020) 3 pgs.
(Continued)

*Primary Examiner* — Pei Yong Weng
(74) *Attorney, Agent, or Firm* — Nicholas Welling; George S. Blasiak; Heslin Rothenberg Farley & Mesiti P.C.

(57) ABSTRACT

Methods, computer program products, and systems are presented. The method computer program products, and systems can include, for instance: obtaining data source data from one or more data source; processing data of the data source data; controlling a smartwatch in dependence on the processing data, wherein the controlling the smartwatch adjusts a flow of air to a smartwatch supporting wrist of a user wearing the smartwatch.

20 Claims, 12 Drawing Sheets

(56) References Cited

OTHER PUBLICATIONS

Myers, Q., "This is What Your Smartwatch is Doing to Your Sad, Chafed Wrist Skin", Mel Magazine, 2021 (retrieved from Internet URL: https://melmagazine.com/en-US/story/apple-watch-smartwatch-rash-itch-bump-red-spots on Mar. 24, 2021) 20 pgs.

Hart, S., "Oppo leak reveals crazy new folding smartwatch design", T3, Jul. 23, 2019 (retrieved from Internet URL: https://www.t3.com/news/oppo-leak-reveals-crazy-new-folding-smartwatch-design on Feb. 13, 2020) 8 pgs.

"Avoid skin irritation from your Samsung smart watch", Samsung (retrieved from Internet URL: https://www.samsung.com/US/support/troubleshooting/TSG01108928/ on Feb. 13, 2020) 2 pgs.

Shukla, V., "Samsung Galaxy Watch Owners Complaining About Rashes, Burns, Skin Reactions", Value Walk, Oct. 15, 2018 (retrieved from Internet URL: https://www.valuewalk.com/2018/10/samsung-galaxy-watch-skin-rashes/ on Feb. 13, 2020) 6 pgs.

Richardson, D., "OPPO's Next Smartwatch Could Have a Rollable Display", Android Headlines, Jul. 23, 2019 (retrieved from Internet URL: https://www.androidheadlines.com/2019/07/oppo-smartwatch-rollable-display.html on Mar. 24, 2021) 8 pgs.

Etherington, D., "Watch The New Phorm iPad Mini Case Generate Physical Keys Out of Thin Air", Feb. 12, 2015 (retrieved from Internet URL: https://techcrunch.com/2015/02/12/tactus-phorm-ipad-mini-case/ on Mar. 14, 2021) 12 pgs.

Welch, C., "LG's groundbreaking roll-up TV is going on sale this year", The Verge, Jan. 7, 2019 (retrieved from Internet URL: https://www.theverge.com/2019/1/7/18171013/lg-rollable-tv-oled-4k-tv-features-photos-video-release-ces-2019 on Mar. 24, 2021) 9 pgs.

\* cited by examiner

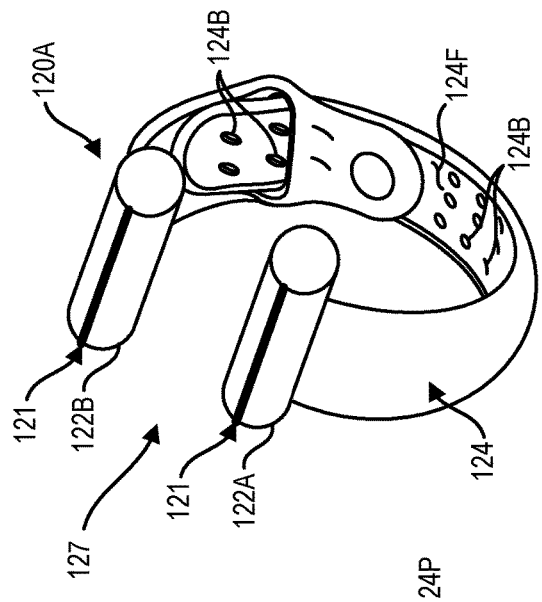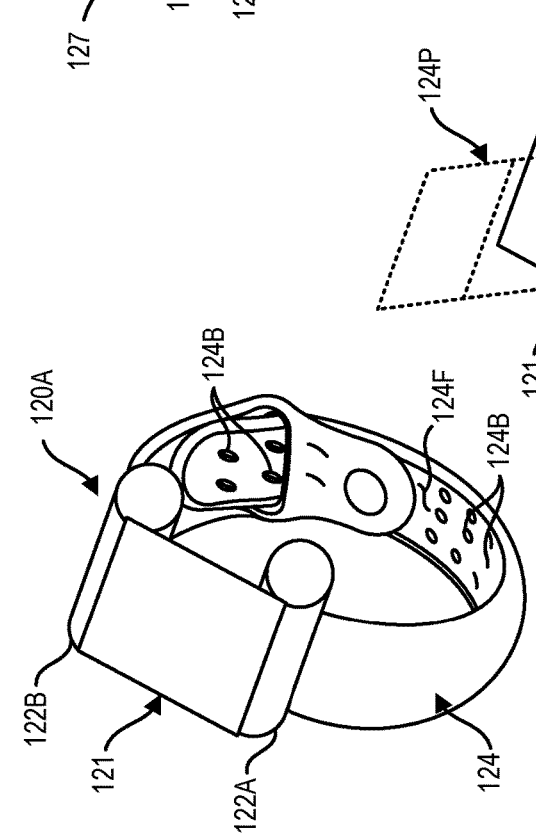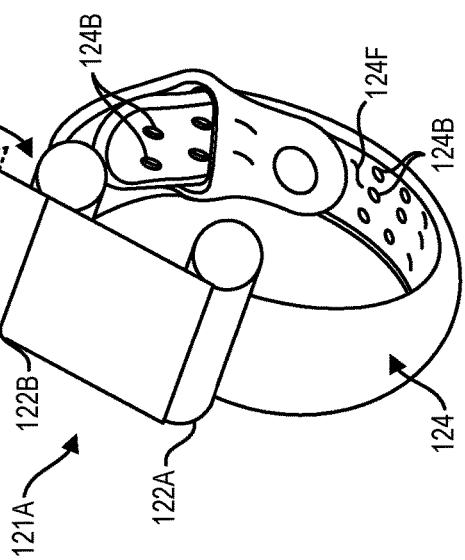

DYNAMICALLY CONTROLLABLE SMARTWATCH

BACKGROUND

The present disclosure relates generally to user equipment devices and in particular to a dynamically controllable smartwatch.

Data structures have been employed for improving operation of computer system. A data structure refers to an organization of data in a computer environment for improved computer system operation. Data structure types include containers, lists, stacks, queues, tables and graphs. Data structures have been employed for improved computer system operation e.g. in terms of algorithm efficiency, memory usage efficiency, maintainability, and reliability.

Artificial intelligence (AI) refers to intelligence exhibited by machines. Artificial intelligence (AI) research includes search and mathematical optimization, neural networks and probability. Artificial intelligence (AI) solutions involve features derived from research in a variety of different science and technology disciplines ranging from computer science, mathematics, psychology, linguistics, statistics, and neuroscience. Machine learning has been described as the field of study that gives computers the ability to learn without being explicitly programmed.

SUMMARY

Shortcomings of the prior art are overcome, and additional advantages are provided, through the provision, in one aspect, of a method. The method can include, for example: obtaining data source data from one or more data source; processing data of the data source data; controlling a smartwatch in dependence on the processing data, wherein the controlling the smartwatch adjusts a flow of air to a smartwatch supporting wrist of a user wearing the smartwatch.

In another aspect, a computer program product can be provided. The computer program product can include a computer readable storage medium readable by one or more processing circuit and storing instructions for execution by one or more processor for performing a method. The method can include, for example: obtaining data source data from one or more data source; processing data of the data source data; controlling a smartwatch in dependence on the processing data, wherein the controlling the smartwatch adjusts a flow of air to a smartwatch supporting wrist of a user wearing the smartwatch.

In a further aspect, a system can be provided. The system can include, for example a memory. In addition, the system can include one or more processor in communication with the memory. Further, the system can include program instructions executable by the one or more processor via the memory to perform a method. The method can include, for example: obtaining data source data from one or more data source; processing data of the data source data; controlling a smartwatch in dependence on the processing data, wherein the controlling the smartwatch adjusts a flow of air to a smartwatch supporting wrist of a user wearing the smartwatch.

Additional features are realized through the techniques set forth herein. Other embodiments and aspects, including but not limited to methods, computer program product and system, are described in detail herein and are considered a part of the claimed invention.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following detailed description taken in conjunction with the accompanying drawings in which:

FIGS. 2A-2D are prospective views of a smartwatch having various display screen configurations;

DETAILED DESCRIPTION

Figure 1:
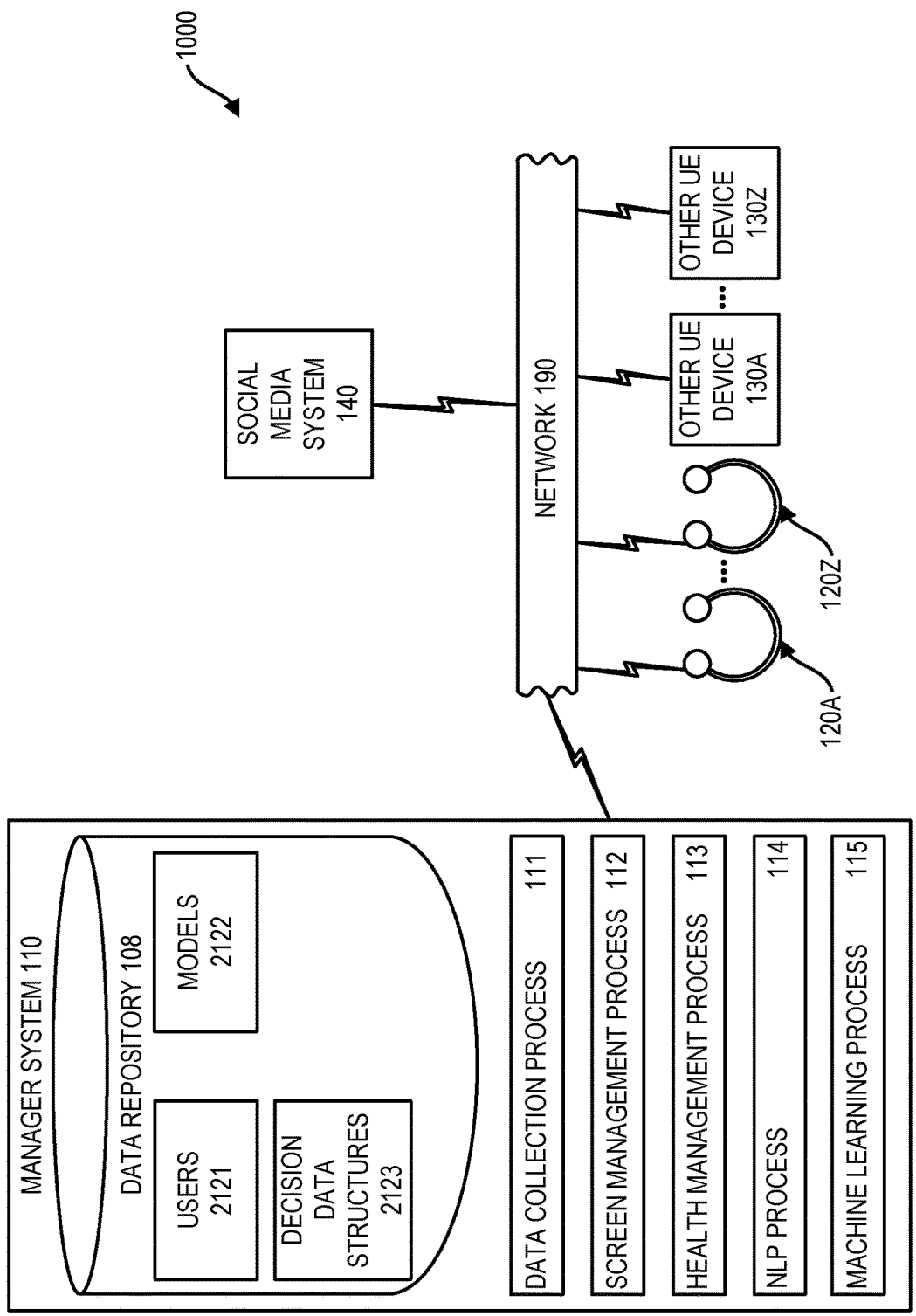
FIG. 1 depicts a system having manager system, smartwatches, other UE devices, and a social media system according to one embodiment.

System 1000 for use in supporting a smartwatch is shown in FIG. 1. System 1000 can include a manager system 110 having an associated data repository 108, smartwatches 120A-120Z, other user equipment (UE devices 130A-130Z), and social media system 140. Manager system 110, smartwatches 120A-120Z, other UE devices 130A-130Z, and social media system 140 can be in communication with one another via network 190. System 1000 can include numerous devices which can be computing node based devices connected by network 190. Network 190 can be a physical network and/or a virtual network. A physical network can be, for example, a physical telecommunications network connecting numerous computing nodes or systems such as computer servers and computer clients. A virtual network can, for example, combine numerous physical networks or parts thereof into a logical virtual network. In another example, numerous virtual networks can be defined over a single physical network. In one embodiment, manager system 110 can be external to smartwatches 120A-120Z, other UE devices 130A-130Z, and social media system 140. According to one embodiment, manager system 110 can be collocated with one or more of smartwatches 120A-120Z, other UE devices 130A-130Z, and/or social media system 140.

Smartwatches 120A-120Z can be particularly configured smartwatches as set forth herein that can be configured to permit regular air flow to the wrist of a user wearing a smartwatch in the wrist area where the watch is worn. Each of the different smartwatches 120A-120Z can be associated to a different user.

Each of the different UE devices 130A-130Z can be associated to a different user. Regarding UE devices 130A-130Z, a UE device of one or more client UE device 130A-130Z, in one embodiment, can be a computing node device provided by a client computer, e.g., a mobile device, e.g. a smartphone or tablet, a laptop, smartwatch or PC that runs one or more program, e.g. including a web browser for opening and viewing web pages.

Data repository 108 of manager system 110 can store various data. In users area 2121, data repository 108 can store data on users of system 1000. System 1000 can be configured so that when a user registers a first smartwatch of the user, system 1000 assigns a universally unique identifier (UUID) to the user. A user can specify permissions to system 1000 when registering as a registered user of system 1000. Permissions can include, e.g., permissions to permit manager system 110 to collect data from the new smartwatch being registered, but also other UE devices of the user such as, e.g., smartphones, televisions, tablets, personal computers, and the like. In users area 2121, data repository 108, for each user of system 1000, can store historical data. Historical data can include, e.g., historical sensor data collected from sensors disposed in smartwatches of a user and other UE devices of a user. Historical data of a user can also include e.g. applications usage data respecting applications that are used by a user that are running on a smartwatch or another UE device of a user. Historical data of users area 2121 can also include historical social media data of a user for respective users of system 1000.

Data repository 108 and models area 2122 can store predictive models of system 1000 that have been trained using historical data of users area 2121 as training data. Predictive models stored in 2122 can be iteratively trained with training datasets defined by historical data stored in users area 2121. Manager system 110 can query trained predictive models stored in models area 2122 for return of action decisions. Action decisions returned by manager system 110 can include, e.g., action decisions to control a display screen or to control the smartwatch's impact on health level of a user. Data repository 108 and decision data structures area 2123 can include one or more decision data structure for return of action decisions. Decision data structures area 2123 can include, e.g., decision tables and decision trees.

Manager system 110 can run various processes. Manager system 110 running data collection process 111 can include manager system 110 collecting data from one or more data source. The one or more data source can include, e.g., smartwatches such as smartwatches 120A-120Z, other UE devices 130A-130Z, and/or social media system 140. When collecting data from a UE device such as a smartwatch or other UE device 130A-130Z, manager system 110 can collect, e.g., sensor output data and/or application usage data. Application usage data can refer to data provided by one or more running application of a UE device such as a smartwatch or other UE device. Manager system 110 running screen management process 112 can control a display screen of smartwatches 120A-120Z. According to one embodiment, a display screen of a smartwatch herein can have a plurality of operating modes.

According to one embodiment, a display screen herein can include a rollable display screen that is retractable into a chamber. According to one embodiment, a smartwatch herein can contain a rollable display screen. According to a hidden display screen configuration herein, a rollable display screen herein can include an entirety of a rollable display screen contained within one or more display screen chamber (cylinder) with no portion of the display screen viewable by a user. According to a standard display screen configuration, a rollable display herein can extend to define an exposed viewing area dimension according to an average sized smartphone. According to a standard display screen configuration, a rollable display screen herein can emulate the appearance of a conventional smartwatch. According to an extended display screen configuration herein, a rollable display screen can be controlled to exhibit an exposed viewing area dimension greater than an exposed viewing area dimension exhibited in a standard display screen operating configuration. According to a limited display screen configuration herein, a rollable display screen can be controlled to exhibit a viewable area having an exposed viewing area dimension less than an exposed viewing area dimension exhibited in a standard display screen operating configuration.

Display screen 121 can be provided using rollable display technology. For configuring display 121 as a rollable display, display screen 121 can be provided using a flexible substrate. A flexible substrate can be formed of e.g., polyimide (PI), polycarbonate (PC), polyethylenapthanate (PEN), cyclic olefin polymer (COP), polyethyleneterephthalate (PET), polynorborneen (PNB), or polyethersulfone (PES). Chamber 122A can include a first roller attaching to a first display screen segment and a first driver motor configured to drive the display screen segment. Chamber 122B can include a second roller attaching to a display screen segment and a second driver motor configured to drive the second display screen segment. Manager system 110, for providing a hidden display screen configuration, can command the first drive motor to wind the first display screen segment entirely into chamber 122A, and can command the second drive motor to wind the second display screen segment entirely into chamber 122B.

Manager system 110 running screen management process 112 can control the viewing area dimension of an exposed display screen herein. Manager system 110 running screen management process 112 can predict a user's usage of a display screen and can control a display screen so that an exposed viewing area dimension of a display screen matches a predicted viewing usage of a user. By matching a display screen configuration to predicted viewing usage, a user need not implement user interface controls for controlling the configuration. By matching a display screen to predicted viewing usage, manager system 110 can regularly control a display screen to be in a hidden or limited display screen configuration and increase airflow to a wrist area of a user wearing a smartwatch.

For predicting a user's usage of a display screen, manager system 110 can query one or more predictive model that predicts the user's usage of a display screen. The one or more predictive model can be trained with training data defined by historical data of the user and in some scenarios the training data can comprise data of other users of system 1000. Where a predictive model is trained with training data associated to a user other than a current user, the predictive model can be regarded to be trained with crowdsourced training data stored in data repository 108.

Manager system 110 running health management process 113 can include manager system 110 controlling an impact of a smartwatch on a health level of a user. Manager system 110 running health management process 113 can include manager system 110 controlling microbumps of smartwatch 120A. Smartwatch 120A, as set forth more fully herein, can include a plurality of microbumps disposed on a wristband of smartwatch 120A-120Z.

Smartwatches 120A-120Z herein can be configured so that a wristband of smartwatch, e.g., smartwatch 120A, makes limited contact with skin in a wrist area of a user that holds a smartwatch. A limited contacting relationship of the wristband to the wrist of a user can permit regular flow of air into the wrist area of a user. The airflow into a wrist area of a user can be further facilitated by the design of a display screen of a smartwatch as set forth herein, including a rollable display which can be rolled into an undisplayed state to maximize airflow into wrist area of a user. Manager system 110 running health management process 113, according to one embodiment, can control the activation states of microbumps of a wristband of a smartwatch of smartwatches 120A-120Z. Manager system 110 running health management process 113, according to one embodiment, can control activation states of microbumps of a wristband so that at any given time, only a subset of microbumps is in an active state, resulting in limited contact of the wristband to a user's skin. Manager system 110 running health management process 113 can include manager system 110 controlling a wristband so that the subset of microbumps that are in an active state at any given time changes through time. For example, at a first time period, a first set of microbumps of smartwatch 120A can be active, and at a next successive time period, the second subset of microbumps can be active. Thus, there can be a reduced or no area of a user's wrist that is persistently contacted by a wristband of a smartwatch during the course of time that the user wears the smartwatch.

The contact between a wristband and the skin of a user's wrist can improve sensing operations. For example, various humidity, temperature, and ultrasound imaging techniques can be improved by contact sensing.

Manager system 110 running health management process 113 can include manager system 110 using various types of historical data such as data collected from, e.g., humidity sensors, ultrasound sensors, temperature sensors, accelerometer sensors and/or camera image sensors. Manager system 110 running health management process 113, according to one embodiment, can include manager system 110 applying a multifactor formula. Manager system 110 running health management process 113, according to one embodiment, can include manager system 110 querying one or more predictive model that is trained with use of training datasets defined by historical data stored in user's area 2121 of data repository 108.

Manager system 110 running natural language processing (NLP) process 114 can include manager system 110 running NLP process 114 to process data for preparation of records that are stored in data repository 108. Manager system 110 can run NLP process 114 for determining one or more NLP output parameter of a message. NLP process 114 can include one or more of a topic classification process that determines topics of messages and output one or more topic NLP output parameter, a sentiment analysis process which determines the sentiment parameter for a message, e.g. polar sentiment NLP output parameters, "negative," "positive," and/or non-polar NLP output sentiment parameters, e.g. "anger," "disgust," "fear," "joy," and/or "sadness" or other classification process for output of one or more other NLP output parameters e.g. one of more "social tendency" NLP output parameter or one or more "writing style" NLP output parameter.

By running of NLP process 114, manager system 110 can perform a number of processes including one or more of (a) topic classification and output of one or more topic NLP output parameter for a received message, (b) sentiment classification and output of one or more sentiment NLP output parameter for a received message, or (c) other NLP classifications and output of one or more other NLP output parameter for the received message.

Topic analysis for topic classification and output of NLP output parameters can include topic segmentation to identify several topics within a message. Topic analysis can apply a variety of technologies, e.g., one or more of Hidden Markov model (HMM), artificial chains, passage similarities using word co-occurrence, topic modeling, or clustering. Sentiment analysis for sentiment classification and output of one or more sentiment NLP parameter can determine the attitude of a speaker or a writer with respect to some topic or the overall contextual polarity of a document. The attitude may be the author's judgment or evaluation, affective state (the emotional state of the author when writing), or the intended emotional communication (emotional effect the author wishes to have on the reader). In one embodiment, sentiment analysis can classify the polarity of a given text as to whether an expressed opinion is positive, negative, or neutral. Advanced sentiment classification can classify beyond a polarity of a given text. Advanced sentiment classification can classify emotional states as sentiment classifications. Sentiment classifications can include the classification of "anger," "disgust," "fear," "joy," and "sadness."

Manager system 110 running NLP process 114 can include manager system 110 returning NLP output parameters in addition to those specification topics and sentiments, e.g., can provide sentence segmentation tags, and part of speech tags. Manager system 110 can use sentence segmentation parameters to determine, e.g., that an action topic and an entity topic are referenced in a common sentence, for example.

Manager system 110 running machine learning process 115 can include manager system 110 iteratively training predictive models stored in models area 2122 of data repository 108. Manager system 110 can be configured so that if new data is collected for storage into data repository 108, the newly stored data is concurrently utilized as training data for training various predictive models stored in models area 2122. Accordingly, models of models area 2122 can be iteratively trained with new training data so that the predictive models remain current and capable of providing predictions based on the latest behaviors exhibited by users.

Social media system 140 can include a collection of files, including for example, HTML files, CSS files, image files, and JavaScript files. Social media system 140 can be a social website such as FACEBOOK® (Facebook is a registered trademark of Facebook, Inc.), TWITTER® (Twitter is a registered trademark of Twitter, Inc.), LINKEDIN® (LinkedIn is a registered trademark of LinkedIn Corporation), or INSTAGRAM® (Instagram is a registered trademark of Instagram, LLC). Computer implemented social networks incorporate messaging systems that are capable of receiving and transmitting messages to client computers of participant users of the messaging systems. Messaging systems can also be incorporated in systems that have minimal or no social network attributes. A messaging system can be provided by a short message system (SMS) text message delivery service of a mobile phone cellular network provider, or an email delivery system. Manager system 110 can include a messaging system, in one embodiment. During a process of registration wherein a user of system 1000 registers as a registered user of system 100, a user sending registration data can send, with permission data defining the registration data, a permission that grants access by manager system 110 to data of the user within social media system 140. On being registered, manager system 110 can examine data of social media system 140, e.g., to determine whether first and second users are in communication with one another via a messaging system of social media system 140. A user can enter registration data using a user interface displayed on a client computer device of client computer devices 130-130Z. Entered registration data can include e.g. name, address, social media account information, other contact information, biographical information, background information, preferences information, and/or permissions data e.g. can include permissions data allowing manager system 110 to query data of a social media account of a user provided by social media system 140 including messaging system data and any other data of the user. When a user opts-in to register into system 1000 and grants system 1000 permission to access data of social media system 140, system 1000 can inform the user as to what data is collected and why, that any collected personal data may be encrypted, that the user can opt out at any time, and that if the user opts out, any personal data of the user is deleted.

Features of smartwatches 120A-120Z are described further in reference to the perspective view of FIG. 2A showing smartwatch 120A which can be representative of the construction of smartwatches 120A-120Z. Smartwatch 120A can include display screen 121 which can be configured as a rollable display screen. Smartwatch 120A can include one or more chambers for storing display screen segments defining a display screen. Smartwatch 120A can include chamber 122A containing a first display screen segment and container and chamber 122B for storing and containing a second display screen segment. Smartwatch 120A can include wristband 124 which can be adapted to be wrapped around a wrist of a user for retention of smartwatch 120A on the wrist of a user. Display screen 121A can be configured as a rollable display screen which, in a displayed configuration, is exposed to an area outside of a chamber and a second configuration in which the display screen is contained within a chamber.

Referring to further aspects of smartwatch 120A, smartwatch 120A can include microbumps 124B formed on an interior (wrist facing) surface of wristband 124 so that when worn by a user, wristband 124 can contact a user's wrist by the action of microbumps 124B. The interior surface can include microbumps 124B and a baseline surface 124F which can face a wrist 129. Baseline surface 124F can be wrist facing and can be defined by the area of the interior surface of wristband not defined by microbumps. Respective ones of microbumps 124B can include an active state and an inactive state. In an inactive state, a microbump 124B does not extend inwardly from baseline (wrist facing) surface 124F of wristband 124. In an active state, a microbump 124B can protrude inwardly from baseline surface 124F to contact a wrist 129.

FIG. 2A depicts smartwatch 120A in a standard operating mode in which display screen 121 features a viewing dimension to extend from a first terminal end of the wristband defined by chamber 122A to a second terminal end of wristband 124 defined by chamber 122B. In the standard operating mode depicted in FIG. 2A, display screen 121 can extend lengthwise and widthwise according to the dimension of an average-sized smartwatch to emulate the operation of a standard size smartwatch.

FIG. 2B illustrates smartwatch 120A in another display screen configuration. FIG. 2B illustrates a hidden display screen configuration. In the display screen configuration depicted in FIG. 2B, display screen 121 can be retracted completely into one or more of chamber 122A and 122B. In one embodiment, display screen 121 can be defined by a single display screen segment. The single display screen segment can be retractable to be fully contained within display screen chamber 122A or chamber 122B. According to one embodiment, display screen 121A can be defined by the combination of a first display screen segment and a second display screen segment. The first display screen segment can be retractable to be contained within chamber 122A, and the second display screen segment can be retractable to be contained within chamber 122B.

An extended screen display configuration is depicted in FIG. 2C. In the extended display screen configuration depicted in FIG. 2C, display screen 121 can be rolled out more extensively to define an extended viewing dimension that is extended lengthwise beyond the length as depicted in the standard display screen configuration of FIG. 2A. In the extended display screen configuration depicted in FIG. 2C, display screen 121 can be rolled out at a distance so that an imaginary vertical plane 121P extending lengthwise with an arm and perpendicularly through a display screen viewing surface will not intersect the wrist of a user. Such a configuration is depicted in FIG. 2C. Display screen 121, as depicted in the extended configuration of FIG. 2C, can be defined by a single display screen segment or multiple display screen segments. In the embodiment in which display screen 121 is defined by a single display screen segment, chamber 122A can roll out the display screen segment into the configuration to define display screen 121 as shown in FIG. 2C. In the embodiment in which display screen 121 is shown in FIG. 2C, as defined by first and second display screen segments, chamber 122A can roll out a first of the display screen segments, and chamber 122B can roll out the second of the display screen segments to define display screen 121 in an extended configuration as depicted in FIG. 2C.

A limited screen display configuration is depicted in FIG. 2C. In the display screen configuration depicted in FIG. 2D, display screen 121 can be rolled out less extensively than the length as depicted in the standard display screen configuration of FIG. 2A. Chamber 122A can roll out the display screen to the length as depicted in FIG. 2D. In the limited display screen configuration as depicted in FIG. 2D, a gap 127 is defined at a top elevation. Gap 127 in FIG. 2D can be delimited on one end by display screen 121 and on another end by an endpoint of wristband 124 defined by chamber 122B.

Figure 2E:
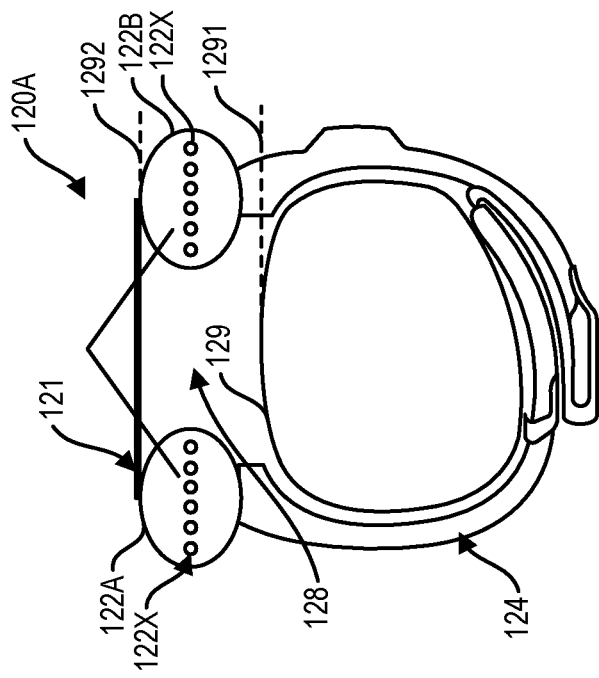
FIG. 2E is a front view of a smartwatch having respective sensor arrays disposed in chambers thereof according to one embodiment.
Figure 2D:
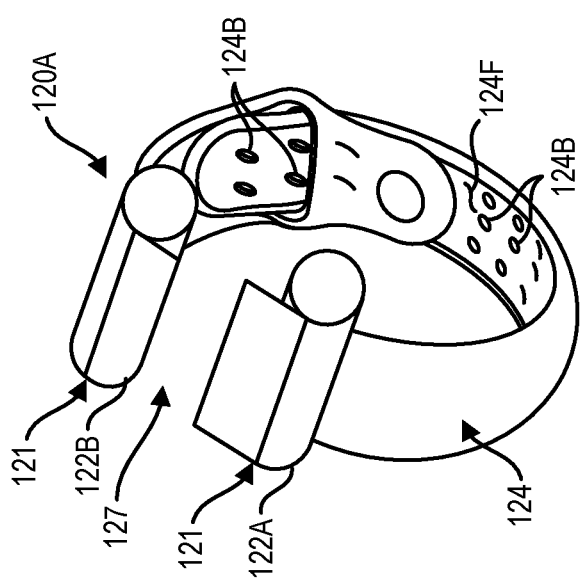

FIG. 2E illustrates a front view of smartwatch 120A worn on a wrist 129 of a user. As best seen in FIG. 2E, wristband 124 can be configured to support chamber 122A and chamber 122B so that both chamber 122A and chamber 122B are fixed above a top elevation of wrist 129. As shown in FIG. 2E, a wrist 129 of a user can have a top elevation 1291, and display screen 121 can have a bottom elevation of elevation 1292 which is an elevation above an elevation of elevation 1291 to define gap 128. Thus, as depicted in FIG. 2C, it is seen that the configuration permits continuous airflow to the top surface of wrist 129 depicted in FIG. 2D. Manager system 110 can increase the continuous flow of air towards the skin surface of a user's wrist unencumbered by display screen 121 by activation of the limited display screen configuration as depicted in FIG. 2D, and further increase airflow to a user wrist 129 by activation of the hidden display screen configuration as depicted in FIG. 2B.

Figure 3A:
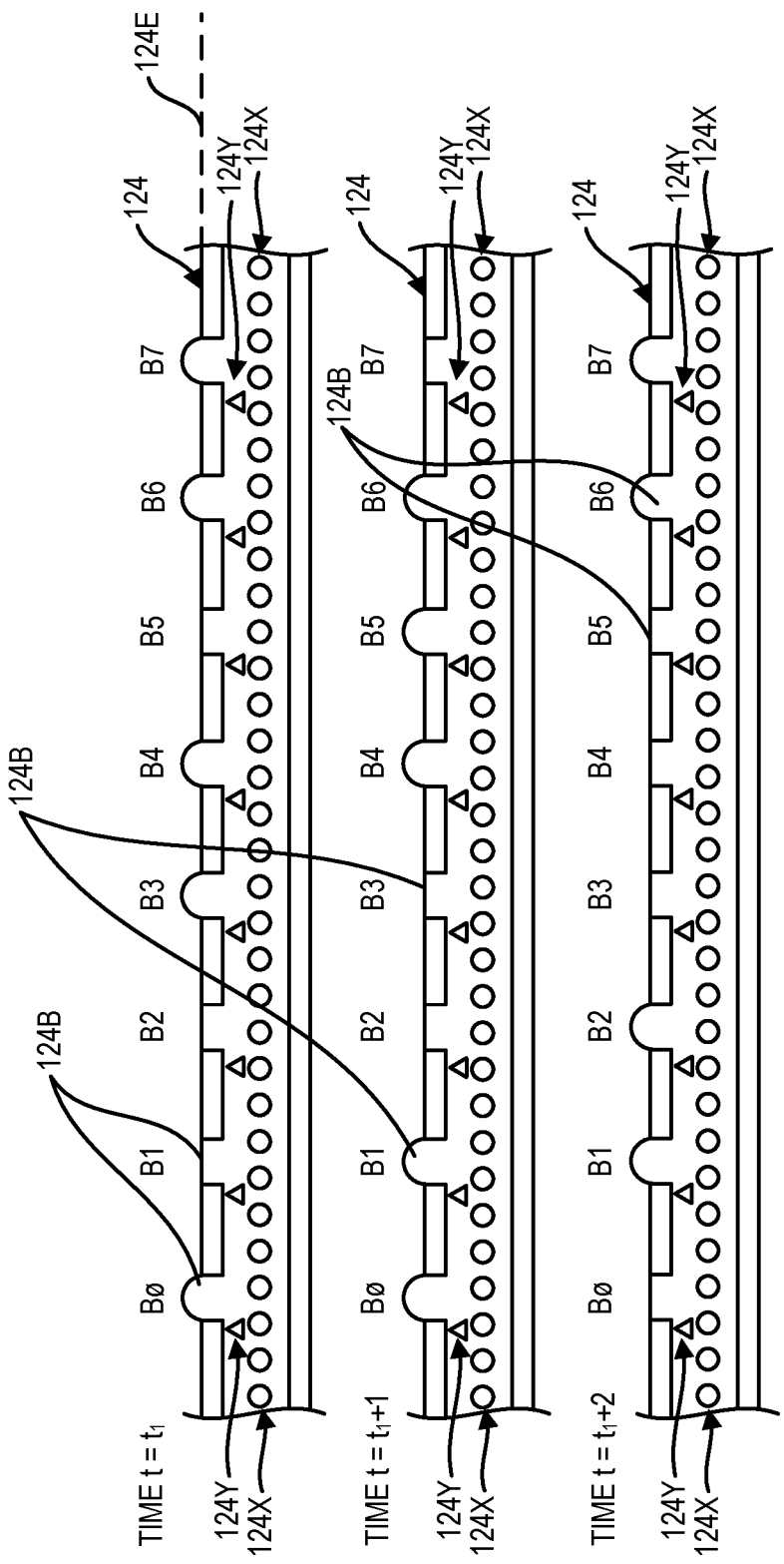
FIG. 3A is a cross-sectional view of a wristband having microbumps defining different patterns of activated microbumps at different times according to one embodiment.
Figure 3B:
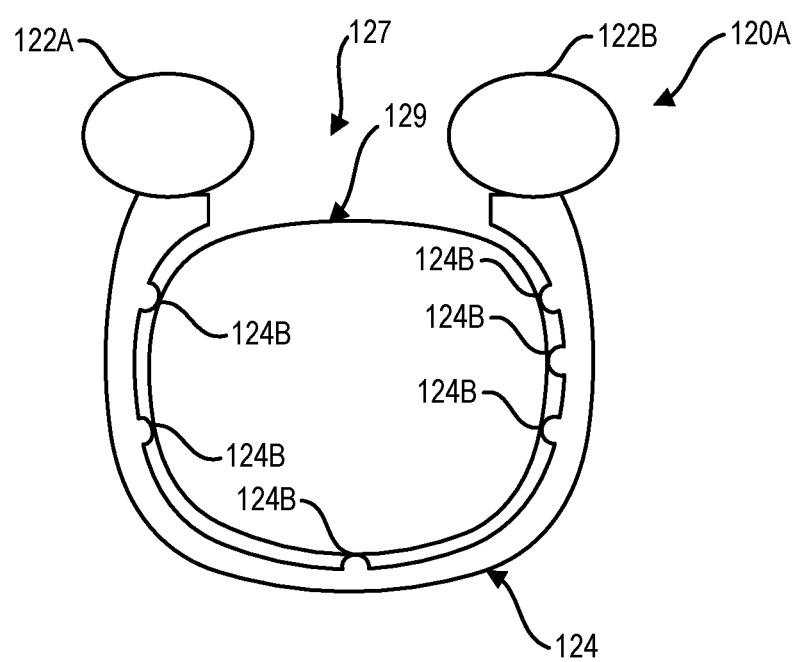
FIG. 3B is a front view of a smartwatch being secured to a user wrist with use of microbumps according to one embodiment.

Aspects of the operation of microbumps formed on an interior (wrist facing) surface of wristband 124 are described in reference to FIGS. 3A and 3B. Referring to FIG. 3A, wristband 124 of smartwatch 120A can be configured so that at any given time that a smartwatch is worn, a subset of microbumps 124B can be active and the particular subset of microbumps that are active can dynamically change over time. For example, referring to FIG. 3A, at time T=T1, microbumps 124B at locations B0, B3, B4, B6, and B7 can be selectively active and the remaining microbumps shown can be inactive. At time T=T1+1, microbumps 124B at locations B0, B1, B4, B5, and B6 can be active and the remaining microbumps shown can be inactive. At time T=T1+2, the microbumps 124B at locations B1, B2, B6, and B7 can be active and the remaining microbumps shown can be inactive. Referring to one aspect, smartwatch 120A can be configured so that at any given time while smartwatch 120A is worn, a user's wrist is contacted by wristband 124 only at locations of a subset of microbumps 124B with the subset dynamically changing over the course of time in which the smartwatch is worn. Referring to FIG. 3B, FIG. 3B depicts smartwatch 120A contacting wrist 129 of a user selectively and only at the location of microbumps 124B that are in an active state.

Dynamically active microbumps can be provided with use of dynamic tactile interface technologies. A dynamic tactile interface can feature a volume of transparent fluid contained within respective microfluidic channels associated to respective microbumps and a displacement device disposed within wristband 124 and/or chamber 122A can displace a portion of the volume of fluid into the channel to transition a deformable region from the inactive state and the active state. A volume of fluid can be controlled to flow through the fluid channel and a variable volume associated to and defining respective microbumps in order to transition the deformable region between the active and inactive states. The volume of fluid can be manipulated by the displacement device to selectively transition a deformable region of a surface of wristband 124 defining a microbump between the active state and the inactive state. For example, a displacement device disposed within wristband 124 and/or chamber 122A can pump fluid into the fluid channel to expand the deformable region thereby transitioning the deformable region from the inactive state into the active state, and the displacement device can pump fluid out of the fluid channel to retract the deformable region thereby transitioning the deformable region from the expanded setting back into the inactive state. The volume of fluid can be substantially transparent, translucent, and/or opaque. According to one embodiment, the volume of fluid can be selected to have an index of refraction to support ultrasound imaging functionally.

Figure 4:
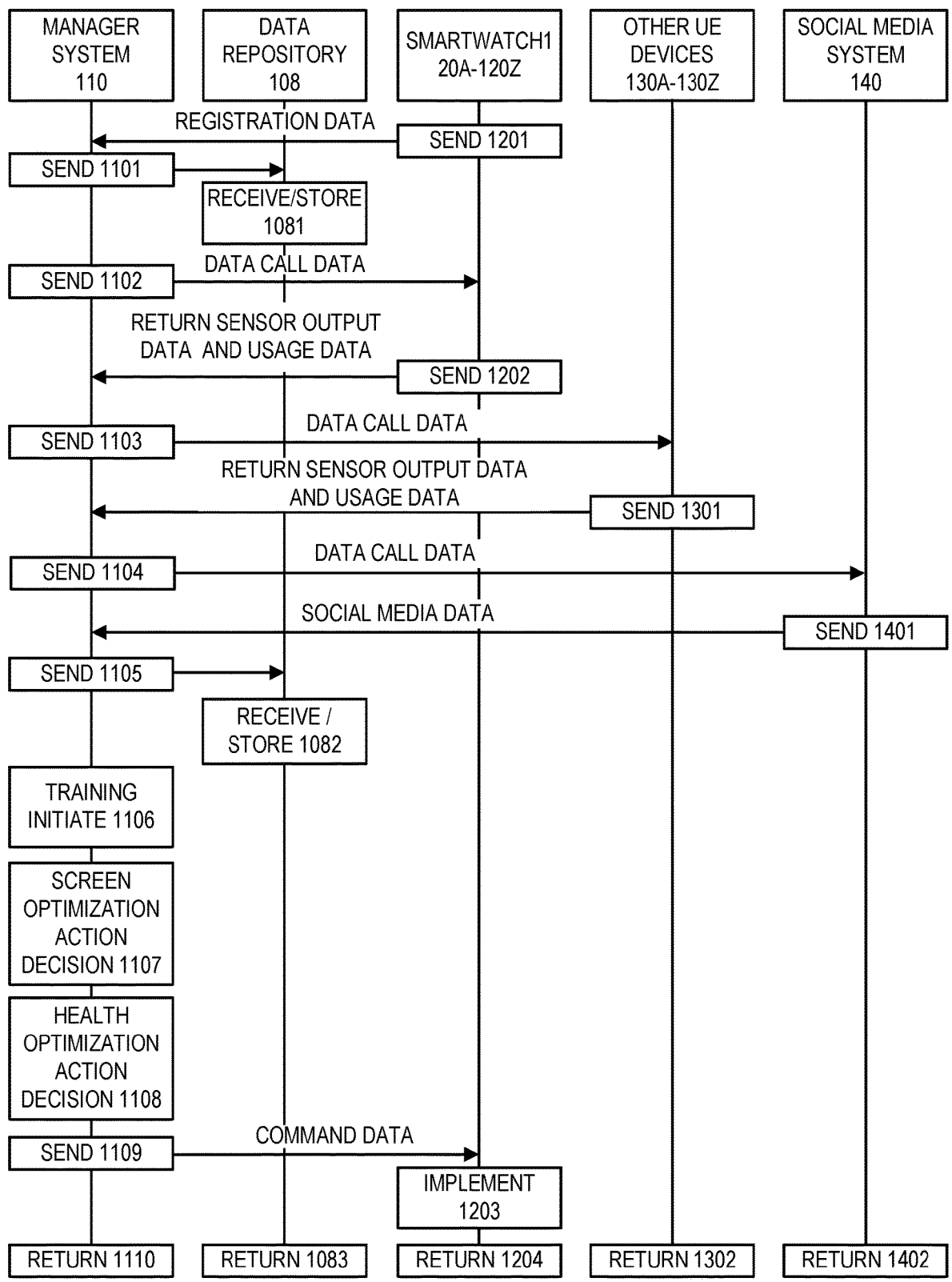
FIG. 4 is a flowchart depicting operation of a manager system interoperating with other components according to one embodiment.

A flowchart illustrating a method for performance by manager system 110 interoperating with smartwatches 120A-120Z and other UE devices 130A-130Z in social media system 140 is described in connection with the flowchart of FIG. 4.

Figure 5:
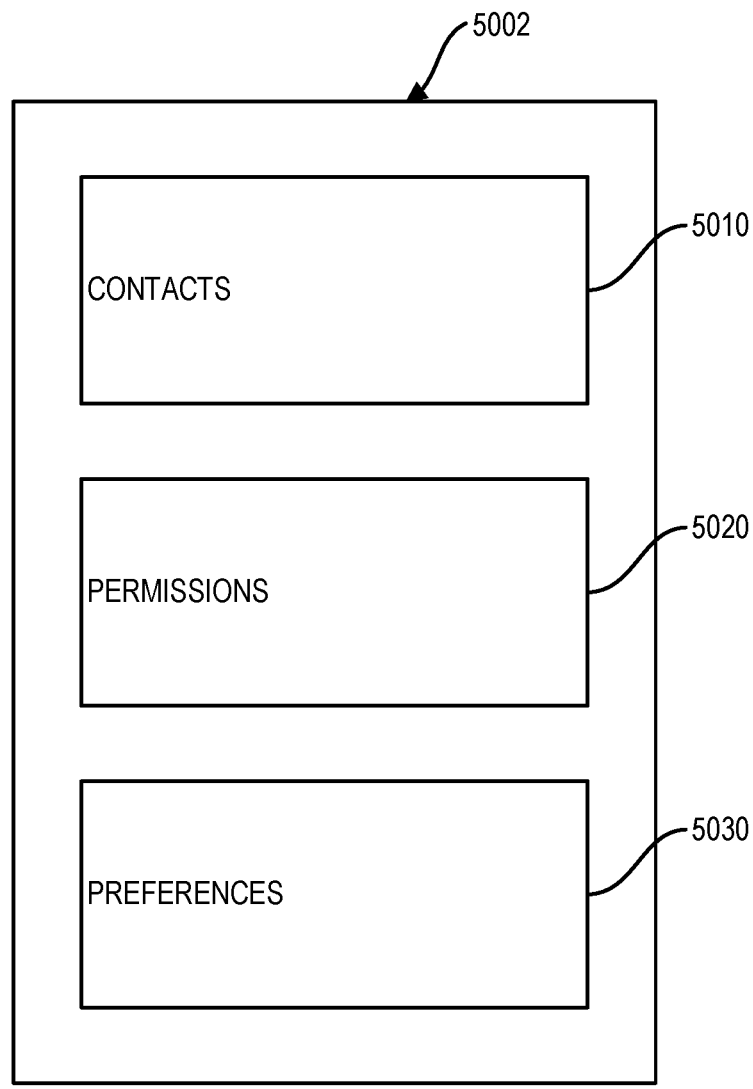
FIG. 5 is a user interface on a display of a UE device according to one embodiment.

At block 1201, smartwatches 120A-120Z, including smartwatch 120A, can be sending registration data for receipt by manager system 110. In response to the receipt of registration data, manager system 110 at block 1101 can send the registration data to data repository 108 for receipt and storage by data repository at block 1081. Registration data sent at block 1201 can include user-defined registration data. The user-defined registration data can be defined by a user, e.g., recent purchaser of a smartwatch. The user can define registration data using a user interface as depicted by user interface 5002 as shown in FIG. 5. As shown in FIG. 5, a user in contacts area 5010 of user interface 5002 can define contacts, e.g., name information, address information, social media account information, email addresses, and the like. In permissions area 5020, a user can define permissions, e.g., permissions that permit manager system 110 to collect and use data of the user for performance of services in connection with the user's use of a smartwatch. Permissions can include, e.g., permissions to use sensor data of a smartwatch of a user and other UE devices of a user in permissions to use application usage data of a smartwatch and other UE devices of a user. Permissions data can also include permissions data specifying permissions to use social media data of a user. In preferences area 5030, a user can define preferences of a user, e.g., likes and dislikes (positive preferences and negative preferences). In preferences area 5030, a user can complete one or more survey that specifies user preferences. In response to the receipt of registration data in the storage of registration data into data repository 108, manager system 110 can assign a user a UUID. The UUID can be associated to a product identifier for the user such as one or more product identifier identifying smartwatch 120A and other UE devices of the user. In response to completion of block 1101, manager system 110 can proceed to block 1102.

At block 1102, manager system 110 can send data call data to smartwatches 120A-120Z and in response to the data call data, smartwatches 120A-120Z at send block 1202 can send return sensor output data and application usage data to manager system 110 for receipt by manager system 110. At block 1103, manager system 110 can send data call data to other UE devices 130A-130Z of users of system 1000, and in response to the receipt of the data call data sent at block 1103, other UE devices 130A-130Z at send block 1301 can send return sensor output and application usage data to manager system 110 for receipt by manager system 110. At block 1104, manager system 110 can send data call data to social media system 140. In response to receipt of the data call data, social media system 140 at block 1401 can send social media data for receipt by manager system 110. At block 1105, manager system 110 can send the received return data sent at block 1301 and block 1401 to data repository 108 for receipt and storage by data repository 108 at block 1082.

With further reference to FIG. 3A, wristband 124 can have disposed therein sensor array 124X as shown in FIG. 3A. Sensor array 124X as shown in FIG. 3A can include a plurality of different types of sensors. Sensors of a first type can be substantially evenly distributed throughout an interior of a housing defined by wristband 124. Sensors of a second type can be distributed substantially evenly throughout the wristband. Sensors of a third type can be distributed substantially spatially evenly throughout an interior of wristband 124. Sensors of a first type can include, e.g., ultrasound sensors for sensing ultrasound images. Sensors of a second type can include, e.g., humidity sensors for sensing humidity. Sensors of a third type can include, e.g., temperature sensors for sensing temperature of a user's skin in a wrist area supporting a watch. Sensors of a fourth type can include, e.g., camera image sensors for sensing anomalous conditions on a user's skin in a wrist area of a user attributable to a rash or other medical skin condition. Referring further to FIG. 3A, wristband 124 can have disposed therein an output device array 124Y comprising output devices of one or more different output device types. According to one embodiment, output device types can include, e.g., micro blowers for blowing air toward an interior defined by wristband 124 heating elements and/or cooling elements.

Referring to FIG. 2D, one or more of chamber 122A or 122B can have disposed therein sensor array 122X. Sensor array 122X can include one or more different types of sensors spatially distributed within the shown chamber. One sensor type that can be disposed within a chamber 122A and/or 122B can be a camera image sensor. A camera image sensor can output image data processible to return a classifier indicating a gaze of a user toward a particular location. A camera sensor output can indicate whether a user wearing smartwatch 120A is gazing or not gazing at a display screen area of smartwatch 120A where the area occupied by display screen 121 is shown in FIG. 2A. Other sensors that can be disposed within chamber 122A and/or chamber 122B can include, e.g., ultrasound sensors, humidity sensors, temperature sensors, and accelerometers.

Sensor output data can define sensor metrics herein. Sensor output data can include raw sensor output data or processed sensor output data processed to return structured data defined by one or more classifier tag. Raw sensor output data from a humidity sensor can be processed to return sensor output data having the classifier tag of dryness level. Raw ultrasound sensor output data can be processed e.g. to return sensor output data having the classifier tag of dryness level based on an impact of perspiration on ultrasound transmissivity. Raw ultrasound sensor output data can be processed, e.g., to return sensor output data having a classifier tag that indicates blood flow and heart rate. Raw ultrasound sensor output data provided by ultrasound image data can be processed, e.g., to return skin condition classifier tags such as a classifier that specifies an anomaly level.

At block 1106, manager system 110 can initiate a next iteration of training of predictive models set forth herein for return of action decisions. Manager system 110 can initiate a next iteration of training at block 1106, and the training can be completed in the background while next processes are performed, such as processes of block 1107 and 1108. At block 1107, manager system 110 can run screen management process 112, FIG. 1, for performance of screen optimization and can return a screen optimization action decision. Manager system 110 at block 1107 can query a trained predictive model such as is described in connection with FIG. 6A.

Figure 6A:
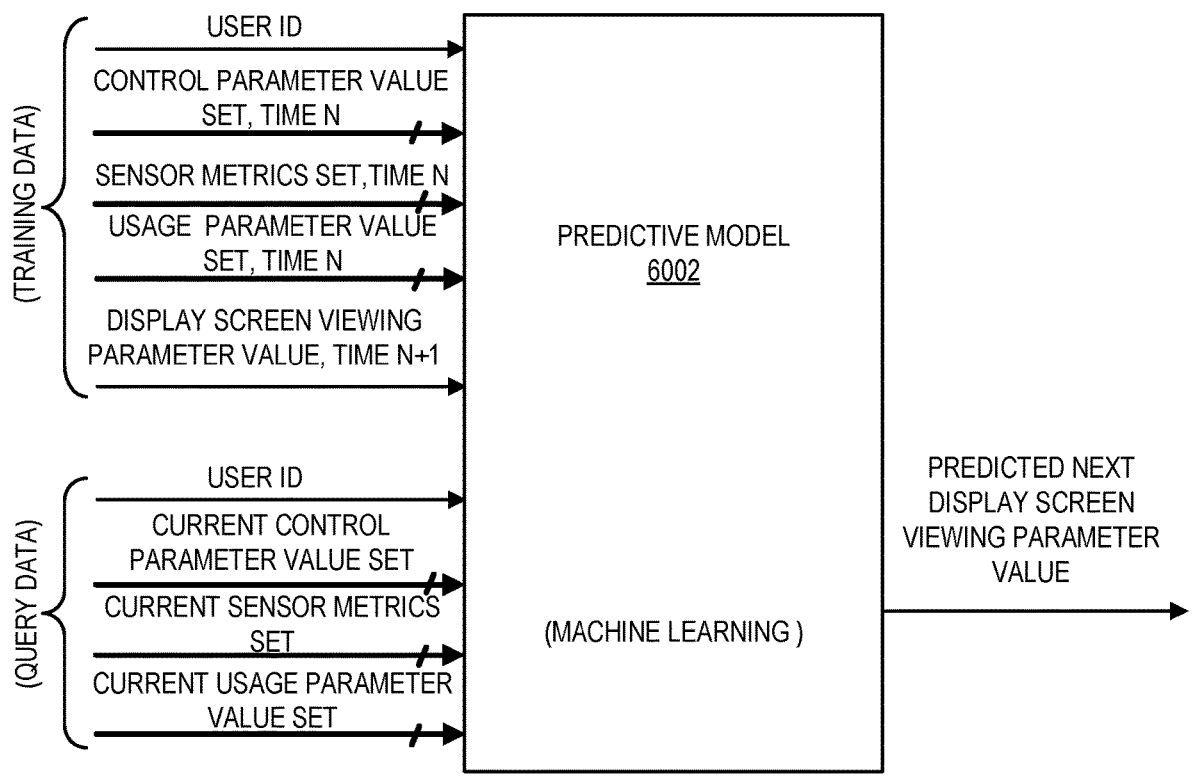
FIG. 6A depicts a predictive model that can be trained with use of machine learning processes according to one embodiment.

Predictive model 6002, as shown in FIG. 6A, can be trained with use of training data defined by historical data stored in users area 2121 of data repository 108. Referring to predictive model 6002, each respective training dataset for training predictive model 6002 can include (A) a set of input parameter values, and (B) an outcome parameter value. A set of input parameter values can include (i) a user ID (which can define an identifier of a smartwatch); (ii) a control parameter value set at time N; (iii) a sensor metrics set at time N; and (iv) an application usage parameter value set at time N. An outcome parameter value defining a training dataset for training predictive model 6002 can include (i) a display screen usage configuration parameter value at time N+1. For each iteratively applied training dataset applied for training of predictive model 6002, the value of N can be incremented. Thus, each iteratively applied training dataset trains an outcome parameter value defined by a display screen viewing parameter value at a subsequent time period on input parameter values associated to a previous time period. Trained as described, predictive model 6002 learns of factors that are predictive and indicative of a user's subsequent viewing usage of a display screen.

By the described training process, predictive model 6002 can be trained to learn a relationship between a current set of input parameter values and a subsequent display screen viewing parameter value. Predictive model 6002 can be trained to predict a user's viewing usage of a display screen at a next period based on current parameter values associated, e.g., to user ID control parameter values, sensor metrics, and application usage parameter values.

Control parameter values of (i) can include, e.g., control parameter values can be controlled specifying current control of smartwatch 120A associated to a current user during a specific time period. Such controls can include controls to control a display screen configuration (control screen configuration setting parameter values), an activation state of microbumps 124B, operation of blowers within wristband 124, and the like.

Parameter values defining (ii) a sensor metrics set can include, e.g., sensor output values from sensor array 124X and sensor output values from other UE devices 130A-130Z associated to a certain user. Sensor output parameter values can also include sensor output values from sensors disposed in other areas of smartwatch 120A such as within chambers 122A and 122B. Sensor output values can include sensor output values that specify a user's gaze on a display screen of a smartwatch. Sensor output values can include raw unstructured output values, and/or structured data values, e.g., classifiers resulting from processing of unstructured data. In one embodiment, sensor output values can include medical skin condition classifiers resulting from processing of camera image sensor data. In one embodiment, sensor output values can include medical skin condition classifiers resulting from processing of camera image sensor data that classifies a medical skin condition in terms of anomaly level. Sensor output data can define sensor metrics herein. Sensor output data can include raw sensor output data or processed sensor output data processed to return structured data defined by one or more classifier tag. Raw sensor output data from a humidity sensor can be processed to return sensor output data having the classifier tag of dryness level. Raw ultrasound sensor output data can be processed e.g. to return sensor output data having the classifier tag of dryness level based on an impact of perspiration on ultrasound transmissivity. Raw ultrasound sensor output data can be processed e.g. to return sensor output data having a classifier tag of that indicates blood flow and heart rate. Raw ultrasound sensor output data provided by ultrasound image data can be processed e.g. to return skin condition classifier tags such as a classifier that specifies an anomaly level.

The training data provided by (iii) usage parameter values at time N can include application usage parameter values obtained from running applications of a smartwatch of a user and other UE devices of a user. Usage parameter values can include data indicating what applications are running during a given time period, and status data associated to the various applications. Embodiments herein recognize that what applications are running can indicate information about a user's current behavior. Applications that can be running can include, e.g., fitness applications, shopping applications, gaming applications, and the like. One usage parameter value can be a real time clock value indicating a time of day, which can be output from any number of applications that send usage data. Embodiments herein recognize that a user's use of a smartwatch can vary depending on time of day and accordingly predictive model 6002 can be trained in one aspect to predict a user's use of a display screen in dependence on a time of day.

The training data provided by usage parameter values at time N (iii) can be replaced or supplemented by topics and/or sentiment parameter values associated to a user at time N for iteratively increasing values of N. Manager system 110, for return of topic and/or sentiment parameter values, can subject one or more data source to natural language processing by running of NLP process (FIG. 1). The one or more data source can include registration data of a user stored in data repository and/or user posts data of social media system 140. Manager system 110 running NLP process 114 can subject survey data of registration data to natural language processing to extract topics indicative of physical activity, e.g., "running," "exercise," and the like, and/or sentiment parameter values, e.g., fear=0.8/1.0. Manager system 110 running NLP process 114 can subject user post data of social media system 140 to national language processing to extract topics indicative of physical activity, e.g. "running," "exercise" and the like, and/or sentiment parameter values, e.g., fear=0.8/1.0. Manager system 110 running NLP process 114 can convert voice inputs captured by a user's smartwatch or other UE device to text and subject the converted text to natural language processing to extract topics indicative of physical activity, e.g. "running," "exercise" and the like, and/or sentiment parameter values, e.g., fear=0.8/1.0. Embodiments herein recognize that an extracted topic parameter value indicative of physical activity can be predictive of a user's viewing usage of the display screen. For example, some users may regularly view biometrics data displayed on a display screen when engaging in physical activity. Embodiments herein recognize that an extracted sentiment parameter value can be predictive of a user's viewing usage of the display screen. For example, some users may regularly view a user interface displayed on a display screen when fearful.

Manager system 110 can use a decision data structure as set forth in Table A to convert a topic or extracted activity classification (extracted from application usage data) to a physical activity level.

TABLE A

| Row | Topic | Physical activity level |
|---|---|---|
| 1 | Running | 0.9 |
| 2 | Reading | 0.1 |
| 3 | Gaming | 0.3 |
| 4 | Driving | 0.3 |
| 5 | Exercise | 0.8 |
| 6 | Eating | 0.4 |

The outcome parameter value (B) (i) (display usage parameter value at time N+1) applied as training data can be provided by adjusting a display screen configuration setting value. According to one embodiment, a display screen as described in connection with FIGS. 2A-2C can have display screen configuration setting values provided on a scale of 0.0 to 2.0 where the configuration value of 0.0 defines a hidden display screen configuration setting (FIG. 2B), where a configuration setting value of 1.0 defines a standard display screen configuration (FIG. 2A), where a display screen configuration setting value of 2.0 defines an extended display screen configuration (FIG. 2E), and where a display screen configuration value of between 0.0 and 1.0 defines a limited configuration setting.

For providing a display screen viewing parameter value for use as training data as described in connection with predictive model 6002, manager system 110 can scale up or scale down such a display screen configuration setting parameter values in dependence on sensor output data. For example, where the display screen configuration setting value is 0.0 to define a hidden display screen configuration and sensor data indicates in the relevant time period that the user was gazing toward the user's smartwatch during the relevant time period, manager system 110 can scale the configuration setting value upward, e.g., to 0.5 based on the sensor data indicating that the user intended to use the smartwatch in the relevant time period. In the case that an actual display screen configuration setting parameter value of a display screen configuration is 1.0, defining a standard use configuration, and during the relevant time period, the user never gazes at the user's smartwatch during the relevant time period based on collected sensor data, manager system 110 can scale the display screen configuration setting value downward, e.g., to 0.5 for providing of a display screen viewing parameter value for use as training data in training predictive model 6002. In the case that an actual display screen configuration setting parameter value of a display screen configuration is 1.0, defining a standard use configuration, and during the relevant time period, the user constantly gazes at the user's smartwatch based on collected sensor data, manager system 110 can scale the display screen configuration setting value upward, e.g., to 1.5 for providing of a display screen viewing parameter value for use as training data in training predictive model 6002. In other embodiments, a display screen configuration setting can be used as a display screen viewing parameter value.

Predictive model 6002, once trained, can respond to query data. A query dataset for using query, predictive model 6002 can include e.g. (i) a user ID, (ii) a current control parameter value set, (iii) a current sensor metric set, and (iv) a current usage parameter value set. Predictive model 6002 in response to the described query data can output prediction data. Prediction data can specify a predicted next display screen viewing parameter values for a current smartwatch, e.g., smartwatch 120A associated to a current user. The predicted next display screen viewing parameter value can specify a predicted viewing usage of the user. Referring again to the flowchart of FIG. 4, manager system 110, at screen optimization action decision block 1107, can query predictive model 6002 to identify a predicted next display screen viewing parameter value for display screen 121 of smartwatch 120A during a next time period. Manager system 110 can then generate command data to implement a display screen configuration in accordance with the predicted next display screen viewing parameter value.

Embodiments herein recognize that based on the training data, querying of predictive model 6002 can return a prediction that specifies a predicted viewing parameter value on a scale of 0.0 (hidden display screen configuration) to 2.0. For example, manager system 110 can return a predicted viewing parameter value of, e.g., 0.3, 1.0, 1.8, 2.0, and the like.

Embodiments herein recognize that different users can tend to look at their smartwatches under different scenarios. For example, a first user might tend to look at their smartwatch frequently when engaging in a web conference detectable as part of application usage data. Other users may tend to look at their smartwatch frequently when running as detectable with use of an accelerometer sensor output. Still other users may tend to look at their smartwatch frequently after being at rest for a substantial amount of time detectable with use of an accelerometer output. Other users may tend to look at their smartwatch frequently when playing a video game (activity classification=gaming) as can be detectable with use of application usage data as set forth herein.

Predictive model 6002 can be trained with training data so that predictive model 6002 for a certain user can predict a usage trend of a certain user with respect to that user's smartwatch, i.e., can predict when that certain user will be viewing data from a display screen of smartwatch 120A.

Predictive model 6002 can be trained with use of all users data, e.g., every user of system 1000. A user ID for use in training predictive model 6002 and for querying predictive model 6002 can be associated to a certain smartwatch identifier. Thus, a user ID can constitute a surrogate identifier for a particular smartwatch. Predictive model 6002 can be configured so that when a predictive model is queried with use of query data that specifies a user ID, predictive model 6002 outputs a prediction for a particular user using a particular smartwatch.

Predictive model 6002 can be configured so that when query data is absent of a user ID, predictive model 6002 can predict a display screen viewing for a next time period of a certain smartwatch based on crowdsource training data of all users. Thus, querying predictive model 6002 with use of a user ID can render a prediction based on a certain user's use and querying predictive model 6002 without a user ID can return a prediction based on crowdsource data. System 1000 can be configured so that early in a deployment period, predictive model 6002 can be queried in a manner to produce a crowdsource data prediction, e.g., with query data absent of user ID and later in a deployment period of a smartwatch when more data on a particular user in a particular smartwatch is accumulated. Predictive model 6002 can be queried to return predictions based on the current user's utilization of a certain smartwatch. Ensemble model techniques can be used for prediction as return based on weighted use of crowdsource based data predictions and individual user prediction data. Manager system 110 on completion of block 1107 can proceed to block 1108.

At block 1108, manager system 110 can run health management process 113 (FIG. 1). At block 1108, manager system 110 can run health management process 113 to determine a health optimization action decision. Such a health optimization action decision can optimize health to a user who is wearing smartwatch 120A. For return of an action decision as indicated at block 1108, manager system 110 can use Eq. 1 as set forth herein below. Eq. 1 can be used to score a predicted performance for each respective microbump 124B of wristband 124 in an active state. Manager system 110 can assign higher than baseline scoring values for microbumps predicted to perform positively when in an active state and can assign lower than baseline scoring values to microbumps predicted to perform negatively when in an active state. Scoring values can be assigned on a scale, e.g., of 0.0 (minimally negative performance) to 1.0 (maximally positive performance). Manager system 110 can score each microbump 124B of wristband 124 using the formula of Eq. 1 below and for each iteration of usage of Eq. 1 can return an ordered list of scoring values ranked from highest scoring to lowest scoring. Manager system 110 can use the ordered list for determination of which microbumps to activate for any given time period of operation of smartwatch 120A. For example, referring again to FIG. 3A, manager system 110 can control microbumps to have differentiated activation patterns at time $T=T_1$, time $T=T_1+1$, and time $T=T_1+2$ as depicted in FIG. 3. Eq. 1 is set forth as follows:

$$S = F_1W_1 + F_2W_2 + F_3W_3 + F_4W_4 + F_5W_5 + F_6W_6 + F_7W_7 + F_8W_8 + F_9W_9 + F_{10}W_{10} + F_{11}W_{11} + F_{12}W_{12} \quad \text{(Eq. 1)}$$

Where S is a predicted performance scoring value assigned by manager system 110 to each microbump of wristband 124 in an active state, where $F_1$-$F_{12}$ are factors contributing to the scoring value and $W_1$-$W_{12}$ are weights associated to the various factors, Eq. 1 can be subject to one or more constraints. For example, one constraint can be that a minimal number of microbumps must be activated at every specific time period of operation of smartwatch 120A. Embodiments herein recognize that in some scenarios, it can be advantageous so that at least a minimal number of microbumps contact a user's wrist 129 at any given point in time. Contacting the user wrist can be advantageous, e.g., for return of accurate sensor data and/or for secure holding of a smartwatch on a user's wrist. Another constraint that can be implemented is that the number of microbumps selected for activation must not exceed a high threshold at every specific time period of operation of smartwatch 120A. Such contact can assure sufficient airflow to a wrist. Another constraint that can be implemented is that the microbumps selected for activation can feature a threshold amount of dispersion through an interior surface of a wristband 124. Another constraint that can be implemented is that a minimal number of microbumps can be aligned with a detected vein of a user for accurate detection of blood flow via ultrasound sensing, for example. In another aspect, system 1000 can be configured so that the constraints themselves can vary over time. For example, system 1000 can be configured so that if natural language processing extracts current topics associated to a user that reference significant physical activity where more perspiration and higher heat is expected, the maximum number of microbumps for activation can be decreased to increase airflow to a user's skin.

Referring further to Eq. 1, factor $F_1$ can be a covered/uncovered factor referring to whether (display screen 121 will be controlled to cover a user's wrist during a next time period in the operation of the smartwatch as determined from block 1107. Manager system 110 can assign higher than baseline scoring values under factor $F_1$ where a user's wrist area will be uncovered by display screen 121, e.g., where display screen 121 is in a hidden display screen configuration and can assign lower than baseline scoring values under factor $F_1$ when the wrist area will be covered by display screen 121 in a next time period. Embodiments herein recognize that if a wrist area will be uncovered by display screen 121, there can be additional air flow to a user's wrist, reducing risk associated to microbump contact.

Referring to factor $F_2$, factor $F_2$ of Eq. 1 can be a staleness factor. Staleness can refer to a length of time in which a current microbump being scored using Eq. 1 has been active and continually contacting a user's wrist. Manager system 110 can assign lower than baseline values under factor $F_2$ where a microbump being scored has been active in contacting a user's wrist for a substantial period of time and can assign higher than baseline scoring values under factor $F_2$ where a microbump is currently not active and not contacting a user's wrist.

Factor $F_3$ can be a dryness factor. Manager system 110 can assign higher than baseline values to a microbump where a skin surface aligned to an associated microbump is currently dry and can assign lower than baseline values to a microbump where the wrist skin of a user aligned to the microbump is currently not dry.

Manager system 110 under factor $F_4$ can assign higher than baseline scoring values under factor $F_4$ where a predicted next time period dryness of a user wrist in an area aligned to a certain microbump being scored is predicted to be dry and can assign lower than baseline scoring values under factor $F_4$ where a predicted dryness of a user's wrist in an area aligned to a current microbump being scored is predicted to be not dry (e.g., threshold exceeding perspiration level) during a next time period. For return of predictions as to next period dryness level (perspiration level), manager system 110 can use predictive model 6004 as set forth herein.

Manager system 110 under factor $F_5$ can assign higher than baseline scoring values under factor $F_5$ where manager system 110 senses cooler temperatures in an area of a wrist aligned to a current microbump being scored and can assign lower than baseline scoring values under factor $F_5$ where manager system 110 detects higher temperatures on a user's wrist in an area aligned to a current microbump being scored.

Manager system 110 under factor $F_6$ can assign higher than baseline scoring values under factor $F_6$ where predicted temperature of an area of a user's wrist aligned to a current microbump being scored is predicted to be lower than a low threshold and can assign lower than baseline scoring values under factor $F_6$ where a next time period temperature of an area of a wrist of a user aligned to a microbump being scored is predicted to be higher than a high threshold.

Manager system 110 can use a predictive model 6004 as described in connection with FIG. 6B in order to make predictions as to future temperatures in areas of a user wrist aligned to certain microbumps of wristband 124.

Manager system 110 under factor $F_7$ can assign higher than baseline scoring values under factor $F_7$ where an anomaly level of a user's wrist in an area aligned to a microbump being scored is lower than a low threshold (indicating, e.g., a non-rash condition) and can assign lower than baseline scoring values under factor $F_7$ where a current anomaly level of a user's wrist in an area aligned to a current microbump being scored exceeds a high threshold (indicating, e.g., a rash condition).

Manager system 110 under factor $F_8$ can assign higher scoring values under factor $F_8$ where a predicted anomaly level during a next time period in the operation of smartwatch 120A is predicted to be lower than a low threshold (indicating, e.g., a predicted non-rash condition) and can assign lower than baseline scoring values under factor $F_8$ where a predicted anomaly level during a next time period is higher than a high threshold (indicating, e.g., a rash condition).

Manager system 110 under factor $F_9$ can assign higher than baseline scoring values under factor $F_9$ where a current heart rate of a user is lower than a low threshold (indicating, e.g., relaxed state of a user) and can assign lower than baseline scoring values under factor $F_9$ where a current heart rate of a user exceeds a high threshold (indicating, e.g., a rash condition). Heartrate sensor output data can be extracted by raw sensor output values from ultrasound sensors of sensor array 124X.

Manager system 110 under factor $F_{10}$ can assign higher scoring values under factor $F_{10}$ where a predicted heart rate during a next time period in the operation of smartwatch 120A is predicted to be lower than a low threshold (indicating, e.g., a relaxed state of a user) and can assign lower than baseline scoring values under factor $F_{10}$ where a predicted heart rate of a user during a next time period exceeds a high threshold (indicative of a stressed state).

Factor $F_{11}$ of Eq. 1 can be a vein alignment factor. Manager system 110 can assign higher than baseline scoring values under factor $F_{11}$ where a microbump being scored is aligned to a vein of a user's wrist and can assign lower than baseline scoring values under factor $F_{11}$ where a microbump being scored is not aligned to user's vein. Embodiments herein recognize that maintaining a minimal number of vein-aligned microbumps can improve sensing of blood flow parameter values.

Factor $F_{12}$ of Eq. 1 can be a natural language processing factor. Manager system 110 can assign higher than baseline scoring values under factor $F_{12}$ where natural language processing indicates a below baseline level of physical activity and can assign a higher than baseline scoring value under factor $F_{12}$ where natural language processing indicates an above baseline level of physical activity. Manager system 110 for assigning scoring values under factor $F_{12}$ can subject data from one or more data source to natural language processing by running of NLP process (FIG. 1). The one or more data source can include registration data of a user stored in a data repository and/or user posts data of social media system 140.

Manager system 110 running NLP process can subject survey data of registration data to natural language processing to extract topics indicative of physical activity, e.g. "running," "exercise," and the like. Manager system 110 running NLP process can subject user post data of social media system 140 to natural language processing to extract topics indicative of physical activity, e.g., "running," "exercise," and the like. Embodiments herein recognize that if a user will be engaging in physical activity there can be a greater risk associated to a microbump contacting a user's wrist.

As noted, sensors of sensor array 124X disposed in wristband 124 can include ultrasound sensors. Ultrasound sensors can include imaging ultrasound sensors that can sense depth and other attributes of user tissue including depth and other attributes of veins of a user. Further, ultrasound imaging processing of a vein area can reveal biometric data such as blood flow parameter values. System 1000 can be configured so that in an initial iteration of health optimization at decision block 1108, manager system 110 can activate ultrasound sensors of sensor array 124X for an extended period to obtain sufficient data such that locations of veins can be ascertained with use of ultrasound imaging techniques. Thus, data can be collected associated to each microbump, indicating vein alignment status of each respective microbump, e.g., aligned with a vein or not aligned with a vein. The collected vein associated attributes can be used in performance of assigning scoring values under factor $F_9$ for each respective microbump of wristband 124. Wristband 124, according to one embodiment, can include between about 2 and 1,000,000 microbumps in one embodiment, between about 2 and 100,000 microbumps, and according to one embodiment, between about 2 and 10,000 microbumps, and according to one embodiment, between about 2 and 1,000 microbumps, and according to one embodiment, between about 2 and 100 microbumps. The microbumps can be substantially evenly distributed throughout an interior wrist facing surface of wristband 124.

Figure 6B:
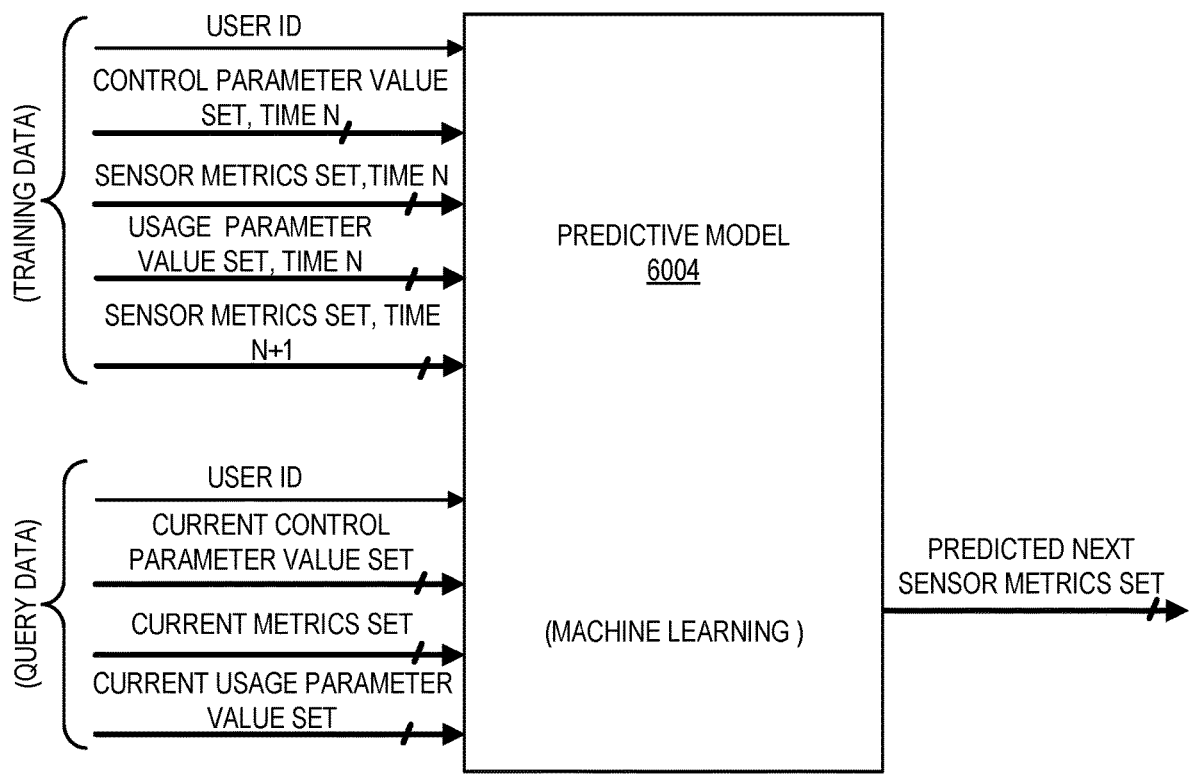
FIG. 6B depicts a predictive model that can be trained with use of machine learning processes according to one embodiment.

For return of predicted dryness, temperature, and skin condition anomaly levels under factors $F_4$, $F_6$, and $F_8$, manager system 110 can query predictive model 6004 as set forth in FIG. 6B. Predictive model 6004 can be trained with use of iteratively applied training datasets. An iteratively applied training dataset can include (A) a set of input parameter values in combination with (B) a set of output parameter values. A set of input parameter values can include (i) a user ID (which can define an identifier of a smartwatch); (ii) a control parameter value set at time N; (iii) a sensor metrics set at time N; and (iv) an application usage parameter value set at time N. An outcome parameter value defining a training dataset for training predictive model 6004 can include (i) a sensor metrics set at time N+1. For each iteratively applied training dataset applied for training of predictive model 6002, the value of N can be incremented.

Thus, each iteratively applied training dataset trains an outcome parameter value defined by a sensor metrics set on input parameter values associated to a previous time period.

By the described training process, predictive model 6004 can be trained to learn a relationship between a current set of input parameter values and a subsequent sensor metrics set at time N+1. Predictive model 6004 can be trained to predict a sensor metrics set associated to a user at a next period based on current parameter values associated, e.g., to a user ID control parameter value, sensor metrics, application usage parameter values, and/or NLP output parameter values.

Control parameter values of (i) can include, e.g., control parameter values can be controlled specifying current control of smartwatch 120A associated to a current user during a specific time period. Such controls can include controls to control a display screen configuration (control screen configuration setting parameter values), an activation state of microbumps 124B, operation of micro blowers within wristband 124 and the like.

Parameter values defining (ii) a sensor metrics set can include, e.g., sensor output values from sensor array 124X and sensor output values from other UE devices 130A-130Z associated to a certain user. Sensor output parameter values can also include sensor output values from sensors disposed in other areas of smartwatch 120A such as within chambers 122A and 122B. Sensor output values can include sensor output values that specify a user's gaze on a display screen of a smartwatch. Sensor output values can include raw unstructured output values, and/or structured data values, e.g., classifiers resulting from processing of unstructured data. In one embodiment, sensor output values can include medical skin condition classifiers resulting from processing of camera image sensor data. In one embodiment, sensor output value can include medical skin condition classifiers resulting from processing of camera image sensor data that classifies a medical skin condition in terms of anomaly level.

The training data provided by (iii) usage parameter values at time N can include application usage parameter values obtained from running applications of a smartwatch of a user and other UE devices of a user. Usage parameter values can include data indicating what applications are running during a given time period, and status data associated to the various applications. Embodiments herein recognize that what applications are running can indicate information about a user's current behavior. Applications that can be running can include, e.g., fitness applications, shopping applications, gaming applications, and the like. One usage parameter value can be a real time clock value indicating a time of day, which can be output from any number of applications that send usage data. Embodiments herein recognize that a user's use of a smartwatch can vary depending on time of day and accordingly predictive model 6002 can be trained in one aspect to predict a user's use of a display screen in dependence on a time of day.

The training data provided by usage parameter values at time N (iii) can be replaced or supplemented by topics and/or sentiment parameter values associated to a user at time N, for iteratively increasing values of N. Manager system 110, for return of topic and/or sentiment parameter values, can subject one or more data source to natural language processing by running of NLP process (FIG. 1). The one or more data source can include registration data of a user stored in data repository and/or user post data of social media system 140. Manager system 110 running NLP process 114 can subject survey data of registration data to natural language processing to extract topics indicative of physical activity, e.g., "running," exercise," and the like, and/or sentiment parameter values, e.g., fear=0.8/1.0. Manager system 110 running NLP process 114 can subject user post data of social media system 140 to natural language processing to extract topics indicative of physical activity, e.g. "running," "exercise," and the like, and/or sentiment parameter values, e.g., fear=0.8/1.0. Manager system 110 running NLP process 114 can convert voice inputs captured by a user's smartwatch or other UE device to text and subject the converted text to natural language processing to extract topics indicative of physical activity, e.g. "running," "exercise," and the like, and/or sentiment parameter values, e.g., fear=0.8/1.0. Embodiments herein recognize that an extracted topic parameter value indicative of physical activity can be predictive of sensor output values. For example, extracted topics indicative of threshold exceeding physical activity can be predictive of increased perspiration represented in sensor metrics. Embodiments herein recognize that an extracted sentiment parameter value can be predictive of next time period exhibited sensor metrics. For example, a threshold exceeding level of fear can be predictive of increased heart rate and increased perspiration represented in sensor metrics.

Training of predictive model 6004 can include training the outcome parameter value (B) (i) (sensor metrics at time N+1) on prior time period input parameter values as set forth herein. Trained as described, predictive model 6004 can learn a relationship between a set of inputs and their impact on future sensor output values as defined by the sensor metric set at time N+1. The described iteratively applied training dataset can be applied for increasing values of N so that predictive model 6004 is trained to learn a relationship between a set of current input values in relation to a subsequent sensor metric set. Embodiments herein recognize that a future dryness (inverse perspiration level), future temperature, and future skin condition anomaly can be dependent on a variety of factors. The described predictive model 6004 can be trained with a plurality of inputs that express the plurality of factors. A sensor metrics set can include parameter values such as blood flow sensing values sensed with use of an ultrasound sensor of sensor array 124X. Embodiments herein recognize that a perspiration level of a user's wrist area can depend on a variety of factors such as heart rate of a user, whether the user is afraid, or whether the user is exercising. The parameter values described in connection with the training data for training predictive model 6004 can express such factors.

Predictive model 6004, once trained, can predict an exhibited dryness (perspiration) level, temperature, and skin condition anomaly level at a particular location of a user's wrist as aligned with and associated to a particular microbump of a wristband 124. Predictive model 6004, once trained, can be subject to a query with use of query data. Query data for use in querying predictive model 6004 can include a dataset which comprises (i) a user ID, (ii) a current control parameter value set, (iii) a current metric set, and (iv) a current application usage parameter value set (and/or a current topic parameter value set). The returned output of predictive model 6004, when subjected to the described query data, can include a predicted next time period sensor metric set for a certain area of a wrist aligned to and associated with a particular microbump of wristband 124 currently being subject to scoring using Eq. 1. Thus, with use of predictive model 6004, manager system 110 can determine whether a particular area of a wrist aligned to a particular microbump is predicted to be dry in a next time period. It can also predict other metrics such as by providing predicted temperature and predicted redness level (indicative of a rash).

Referring to predictive model 6004 and factors $F_3$, $F_5$, $F_7$, and $F_9$, manager system 110 can predict an adrenaline surge exhibited by a user. During an adrenaline surge, the following can occur: (a) eyes dilate; (b) heart beats faster; (c) sweat increases; (d) bronchioles dilate (so more oxygen is obtained); (e) blood vessels dilate (enlarge) in our muscles; (f) blood vessels constrict in our digestive tract to slow digestion (g) kidneys make more renin (to increase blood pressure) (g) glucose production increases, for energy.

Depending on the configuration of system 1000, system 1000 can detect some or all of the noted symptoms of an adrenaline rush, and system 1000 using predictive model 6004 can predict some or all of the noted symptoms. With historical learning, system 1000 can be predicting the adrenal hormone secretion timeline (e.g. based on parameter values indicating the threshold exceeding fear or any change in physiological parameters) and based on such, predicting manager system 110 can dynamically control an activation pattern of microbumps 124B.

At action decision block 1108, manager system 110 can return an action decision to generate command data. With use of Eq. 1 and predictive model 6004, manager system 110 can generate an ordered list of microbumps. Based on the ordered list, manager system 110 can generate command data for commanding activation of top ranked microbumps according to the ordered list. As noted, the ordered list can be subject to various constraints, including constraints involving minimal number, maximum number, spatial distribution of microbumps, and the like. After generation of such command data, manager system 110 can proceed to block 1109. At block 1109, manager system 110 can send command data to smartwatch 120. In response to the received command data, smartwatch 120A at block 1203 can implement the command data, e.g., to activate select microbumps as identified at health optimization action decision block 1108.

Predictive model 6004 can be configured so that when query data is absent of a user ID, predictive model 6004 can predict a display screen viewing for a next time period of a certain smartwatch based on crowdsource training data of all users. Thus, querying predictive model 6004 with use of a user ID can render a prediction based on a certain user's use and querying predictive model 6004 without a user ID can return a prediction based on crowdsource data. System 1000 can be configured so that early in a deployment period, predictive model 6004 can be queried in a manner to produce a crowdsourced data prediction, e.g., with query data absent of user ID and later in a deployment period of a smartwatch when more data on a particular user in a particular smartwatch is accumulated. Predictive model 6004 can be queried to return predictions based on the current user's utilization of a certain smartwatch. Ensemble model techniques can be used for prediction as return based on weighted use of crowdsource based data predictions and individual user prediction data.

On completion of send block 1109, manager system 110 can proceed to return block 1110. At return block 1110, manager system 110 can return to block 1102. At block 1102, manager system 110 can send a next iteration of data call data to smartwatch 120A-12Z for return of a next iteration of sensor output data and application usage data from at least one smartwatch, e.g., smartwatch 120A. It will be seen, with reference to the flowchart of FIG. 4, that manager system 110 can iteratively perform the loop of blocks 1102-1110 during a deployment period of smartwatch 120A. With each iteration of the loop of blocks 1102-1110, manager system 110 can retrain predictive models, such as predictive model 6002 and predictive model 6004 with training data defined by newly received sensor output data and application usage data. At each iteration of block 1107, manager system 110 can generate command data for providing a certain display screen configuration, e.g. a hidden display screen configuration, limited display screen configuration, a standard display screen configuration, or an extended display screen configuration. At each iteration of health optimization action decision block 1108, manager system 110 can generate a next iteration of command data for controlling activation states of respective microbumps 124B. Manager system 110 at send block 1109 can iteratively apply command data for providing a certain display screen configuration and a certain microbump pattern. It will be seen with reference to the loop of blocks 1102-1110 and FIG. 3A, that manager system 110 can iteratively change a pattern of active microbumps over time so that a subset of microbumps that are currently active dynamically change over time. The dynamic changing of microbumps can be provided to avoid the user being contacted by wristband 124 at a certain focus location for extended periods. Rather, the contact points at which wristband 124 contacts a user's wrist can dynamically change to increase the health of a user.

In one embodiment, manager system 110 can monitor the aggregate score of each microbump of wristband 124 under Eq. 1. Given that the score, S, for each microbump specifies predicted performance of microbumps in an active state, which is an indication of a capacity of skin to tolerate contact, the aggregate score can provide an indication of the overall health of a user's wrist. In one embodiment, manager system 110 can be configured so that responsively to the aggregate score falling below a low threshold, manager system 110 can activate output device array 124Y provided by micro blowers, to increase the capacity of a user's skin to tolerate contact. In one embodiment, manager system 110 can be configured so that responsively to the aggregate score falling below a low threshold, manager system 110 can decrease a maximum number of microbumps that can be activated at any given time period. In one embodiment, manager system 110 can be configured so that responsively to the aggregate score exceeding a high threshold, manager system 110 can deactivate output device array 124Y provided by microblowers. In one embodiment, manager system 110 can be configured so that responsively to the aggregate score exceeding a high threshold, manager system 110 can increase a maximum number of microbumps that can be activated at any given time period.

Various available tools, libraries, and/or services can be utilized for implementation of predictive model 6002 and/or predictive model 6004. For example, a machine learning service can provide access to libraries and executable code for support of machine learning functions. A machine learning service can provide access to a set of REST APIs that can be called from any programming language and that permit the integration of predictive analytics into any application. Enabled REST APIs can provide e.g. retrieval of metadata for a given predictive model, deployment of models and management of deployed models, online deployment, scoring, batch deployment, stream deployment, monitoring and retraining deployed models. According to one possible implementation, a machine learning service provided by IBM® WATSON® can provide access to libraries of APACHE® SPARK® and IBM® SPSS® (IBM® WATSON® and SPSS® are registered trademarks of International Business Machines Corporation and APACHE® and SPARK® are registered trademarks of the Apache Software Foundation. A machine learning service provided by IBM® WATSON® can provide access to a set of REST APIs that can be called from any programming language and that permit the integration of predictive analytics into any application. Enabled REST APIs can provide e.g. retrieval of metadata for a given predictive model, deployment of models and management of deployed models, online deployment, scoring, batch deployment, stream deployment, monitoring and retraining deployed models. Training of predictive model 6002 and/or predictive model 6004 can include use of e.g. support vector machines (SVM), Bayesian networks, neural networks, and/or other machine learning technologies.

At return block 1083, data repository 108 can return to a stage preceding block 1082 to receive additional returned sensor output, application usage data, and returned social media data. Referring to smartwatches 120A-120Z, the at least one smartwatch, on completion of implement block 1203, can proceed to block 1204. At block 1204, the at least one smartwatch can return to a stage preceding block 1202 in order to respond to received data call data so that the at least one smartwatch can send return sensor data and application usage data to manager system 110 at block 1202. Referring to other UE devices 130A-130Z, other UE devices 130A-130Z at return block 1302 can return to a stage preceding block 1301 so that the other UE devices 130A-130Z are able to respond to data call data sent at block 1103 and respond at block 1301 to such data call data to return sensor output data and application usage data at block 1301. Social media system 140 at return block 1402 can return to a stage preceding block 1401 so that social media system 140 is able to respond to data call data sent by manager system 110 at block 1104 in order for social media system 140 at block 1401 to send social media data to manager system 110.

There is set forth herein a method and system by which touch area on the skin can be reduced, and based on skin parameter analysis, the touch location on the skin can be changed dynamically, so that perspiration ducts are not covered. Embodiments herein recognize that some users may experience discomfort or skin irritation when wearing the smartwatch for prolonged periods. Embodiments herein recognize, for example, that when a smartwatch wristband is covering the wrist skin, then perspiration ducts can be blocked. Blocking of wrist skin can cause rashes in the skin. Embodiments herein also recognize that if a user wears a smartwatch too tightly or loosely for an extended period, various problems could arise such as redness, itchiness, swelling, and irritation. Embodiments herein recognize that in some scenarios, perspiration, water, soap, and other irritants get trapped against a wearer's skin under the device, causing skin reactions. If the wristband is too tight, it could block the perspiration ducts. If the wristband is too loose, the wristband can slide on a wrist to cause further irritation. Embodiments herein recognize that when a user wears a smartwatch, the smartwatch can be covering the skin surface around the wrist, and hence perspiration ducts can be blocked to potentially cause skin rashes. Embodiments herein provide a method and system by which a smartwatch wristband can be controlled to avoid blocking the perspiration ducts of any user when he wears the smartwatch. Accordingly, the skin surface will not be blocked and hence there will not be any change of skin rashes.

According to another aspect, a smartwatch display screen can be dynamically controlled in dependence on predicting a user's need to look at the display area of smartwatch. According to one aspect, an area occupied by a display screen can be moved to increase airflow to a user's skin.

A smartwatch display screen can be configured as a rollable display screen. Based on predicted viewing use of a user, a display screen can be unrolled and display viewing area defined by the display screen be created for smartwatch. Based on a user's predicted viewing use, the rollable display area can be expanded with use of first and second chambers which can be provided as cylindrical chambers, each of which can have a roller for winding and unwinding a display screen segment. A system can be configured to iteratively predict a user's viewing use of a smartwatch and can apply command data so that viewing area of the display screen matched the predicted viewing use.

The inner (wrist facing) surface of a smartwatch can include microbumps with activation states controllable within use of microfluidic features defined within a housing. A system herein can control the microfluidic features to dynamically change the position of the microbumps to thereby alter the position of the smartwatch's contact area with skin. The smartwatch can be controlled so that a user's wrist is absent of an area that is continually contacted during a wear period of a smartwatch.

A smartwatch wristband can have incorporated therein a plurality of sensors. The plurality of sensors can include, e.g., humidity sensors, temperature sensors, ultrasound sensors, and/or camera image sensors. The sensors can output sensor parameter values provided, e.g., by a perspiration level at a particular location on a wrist (defining with other locations a perspiration spatial pattern), temperature at a particular location on a wrist (defining with other locations a temperature spatial pattern), and skin condition anomaly level at a particular location on a wrist (defining with other locations a skin condition anomaly spatial pattern). A system herein can determine current sensor output parameter values, and, with use of a trained predictive model, can predict sensor output values at a next time period. A system herein can use current sensor output parameter values and/or predicted next time period sensor output parameter values to adjust to iteratively adjust a spatial pattern defined by active state wristband microbumps.

A smartwatch wristband can incorporate an ultrasound scanning module which can scan the position of the vein, and accordingly, can identify an appropriate portion on a wristband where microbumps will be activated, so with minimum touch, biometric data can be gathered, and the touch area will dynamically be changing. Using historical learning, a smartwatch herein will know when a display screen viewing area should be created based on a user's predicted viewing use. When a system herein predicts that a user wants to view a display screen, the system can command a smartwatch to unroll a display screen to define an exposed viewing area of a display screen. The position, dimension, and shape (touch area with wrist) of activated microbumps can be provided based on a perspiration pattern so that one area is not covered for an entirety of a smartwatch wearing session.

A system herein can be configured to track any irritation in the skin because of applied pressure. The frequency and density of microbumps that are activated can be determined dynamically based on a tracked current health condition of a user. System 1000 can be configured so that if the health condition of a user is poor, then continuous biometric data gathering will be required. Activities of a user can be tracked, e.g., with use of application usage data, and/or natural language processing output parameter values. Historical activities defining historical data can be used to train predictive models. Activities that can be tracked can include activities that are stressful, or which have a threshold exceeding physical activity level. A system herein can control a display screen and/or a wristband of a smartwatch in dependence on tracked activities of a user.

According to one embodiment, a wristband can include an array of output devices provided by an array of microblowers configured to blow air through gaps defined amongst microbumps of a wristband. According to one embodiment, a system herein can control such microblowers dynamically in dependence on detected conditions.

Embodiments herein can feature a rollable display screen defining an adjustable viewing area. A system herein can be configured so that when smartwatch display screen is not used for viewing, the display screen can be controlled to be in a hidden or limited display screen configuration to define a gap in an area that can be occupied by a display screen, resulting in increased airflow to a wrist.

A system herein can be configured so that when a user wants to view a display screen, the system can apply command data for rolling out a rollable display screen to define an exposed viewing area for a user to view.

Rolling out of a screen display can be expanded to increase a dimension of an exposed viewing area. The wristband of a smartwatch will be having microfluidics-based microbumps, and the same microbumps can be programmatically be created. The microbumps can be touching on the wrist skin, and from time to time, the touch position can also change. A system can be configured so that a certain area of skin on a wrist will not be persistently covered during a wearing session of a smartwatch. Accordingly, airflow is encouraged, and a perspiration duct will not be covered. The touch location on the skin of a wrist area can be changed from time to time.

A wristband herein can include microfluidic layers which incorporate various sensors, e.g., humidity sensors, temperature sensors, ultrasound sensors, and camera image sensors. When a user wears a smartwatch, then the belt area will be identifying the touch location dynamically. The sensor feed from the wristband will be identifying any change in sensor output parameter values specifying a skin attribute and will be tracking the perspiration generation pattern in the smartwatch. A system can be configured to identify the microfluidics channels for activation of a microbump, and how microbumps will be created to touch the skin surface.

A smartwatch can be identifying how the touch position on the skin area needs to be changed, and accordingly identifying microfluidics channels to control for activation of select microbumps touching on the skin surface. The smartwatch wristband can include ultrasound sensors for ultrasound scanning, and based on an ultrasound scan, a vein position can be identified. A system can be configured so that a minimal number of microbumps are in contact with a vein location of a wrist for accurate sensing of heart rate also by ultrasound.

Based on the position of the vein, appropriate locations on an inner (wrist facing) surface of a wristband can be selectively activating select microbumps for touching on the skin surface. A display screen can be defined by a rollable display screen, and the same will be rolled and contained in one or more chamber such as a cylindrical chamber.

When a user needs the display area is to be created, then the display area will be created dynamically, and accordingly, the user can view the display area. Using historical learning, the smartwatch will be identifying when the user needs to view the display area of the smartwatch and accordingly, the display area will be unrolled from the rollable cylinder When the smartwatch detects the user wants to look at the smartwatch display, then the rollable display area will be expanded and the user can view the required content in the display screen.

Certain embodiments herein may offer various technical computing advantages involving computing advantages to address problems arriving in the realm of computer systems. Embodiments herein can involve improvements to computer systems, particularly in the realm of smartwatch computer systems. Embodiments herein can include features for predicting a user's display screen viewing of a smartwatch and can responsively generate a prediction as to subsequent use of applied command data for changing a display screen configuration of a smartwatch. Embodiments herein can include controlling a smartwatch to exhibit different display screen configurations such as a hidden display screen configuration, a limited display screen configuration, a standard display screen configuration, and an extended display screen configuration. Embodiments herein can predict physiological data associated to a user's wearing of a smartwatch. Embodiments herein can include a smartwatch wristband featuring microbumps that can be selectively activated to establish contact between a wristband and a user's wrist at selected locations. Embodiments herein can feature control of such microbumps so that at a given time, only a subset of microbumps of a wristband contact a user's wrist and further, so that a particular subset of microbumps which contact a user's wrist at any particular time changes dynamically over time. Embodiments herein can include predicting the level of perspiration on a user's wrist and can responsively control a smartwatch to optimize health and comfort to a user in dependence on the predicted perspiration level. Embodiments herein can include predicting a physiological parameter value associated to a user and can responsively control a smartwatch to optimize health and comfort to a user in dependence on the predicted physiological parameter value. Various decision data structures can be used to drive artificial intelligence (AI) decision making, such as a decision data structure that cognitively maps topics to physical activity levels. Decision data structures as set forth herein can be updated by machine learning so that accuracy and reliability is iteratively improved over time without resource consuming rules intensive processing. Machine learning processes can be performed for increased accuracy and for reduction of reliance on rules based criteria and thus reduced computational overhead. For enhancement of computational accuracies, embodiments can feature computational platforms existing only in the realm of computer networks such as artificial intelligence platforms, and machine learning platforms. Embodiments herein can employ data structuring processes, e.g., processing for transforming unstructured data into a form optimized for computerized processing. Embodiments herein can examine data from diverse data sources such as mobile device sensors, mobile device applications, and social media servers. Embodiments herein can include artificial intelligence processing platforms featuring improved processes to transform unstructured data into structured form permitting computer based analytics and decision making. Embodiments herein can include particular arrangements for both collecting rich data into a data repository and additional particular arrangements for updating such data, and for use of that data to drive artificial intelligence decision making. Certain embodiments may be implemented by use of a cloud platform/data center in various types including a Software-as-a-Service (SaaS), Platformas-a-Service (PaaS), Database-as-a-Service (DBaaS), and combinations thereof based on types of subscription.

Figure 7:
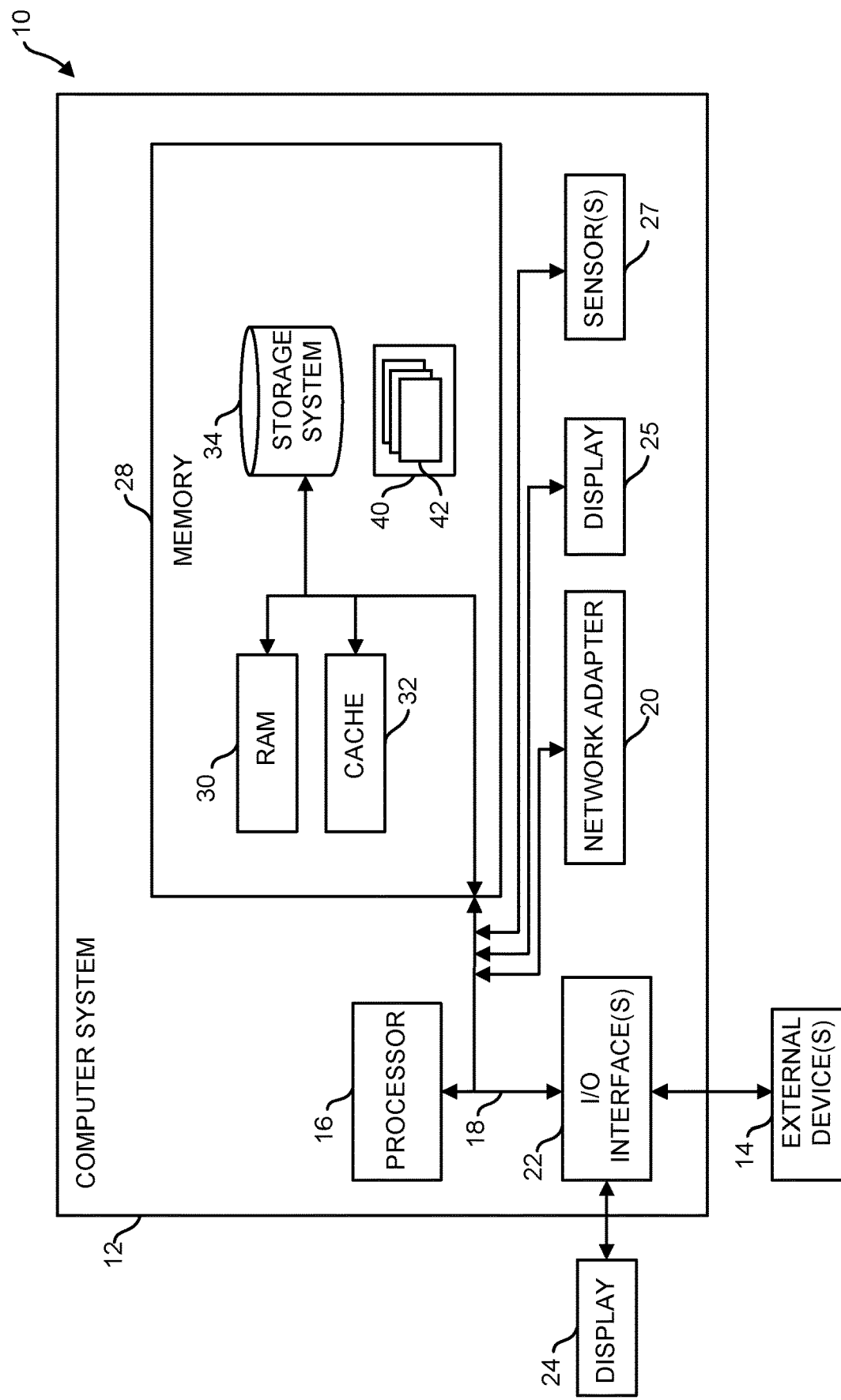
FIG. 7 depicts a computing node according to one embodiment.
Figure 8:
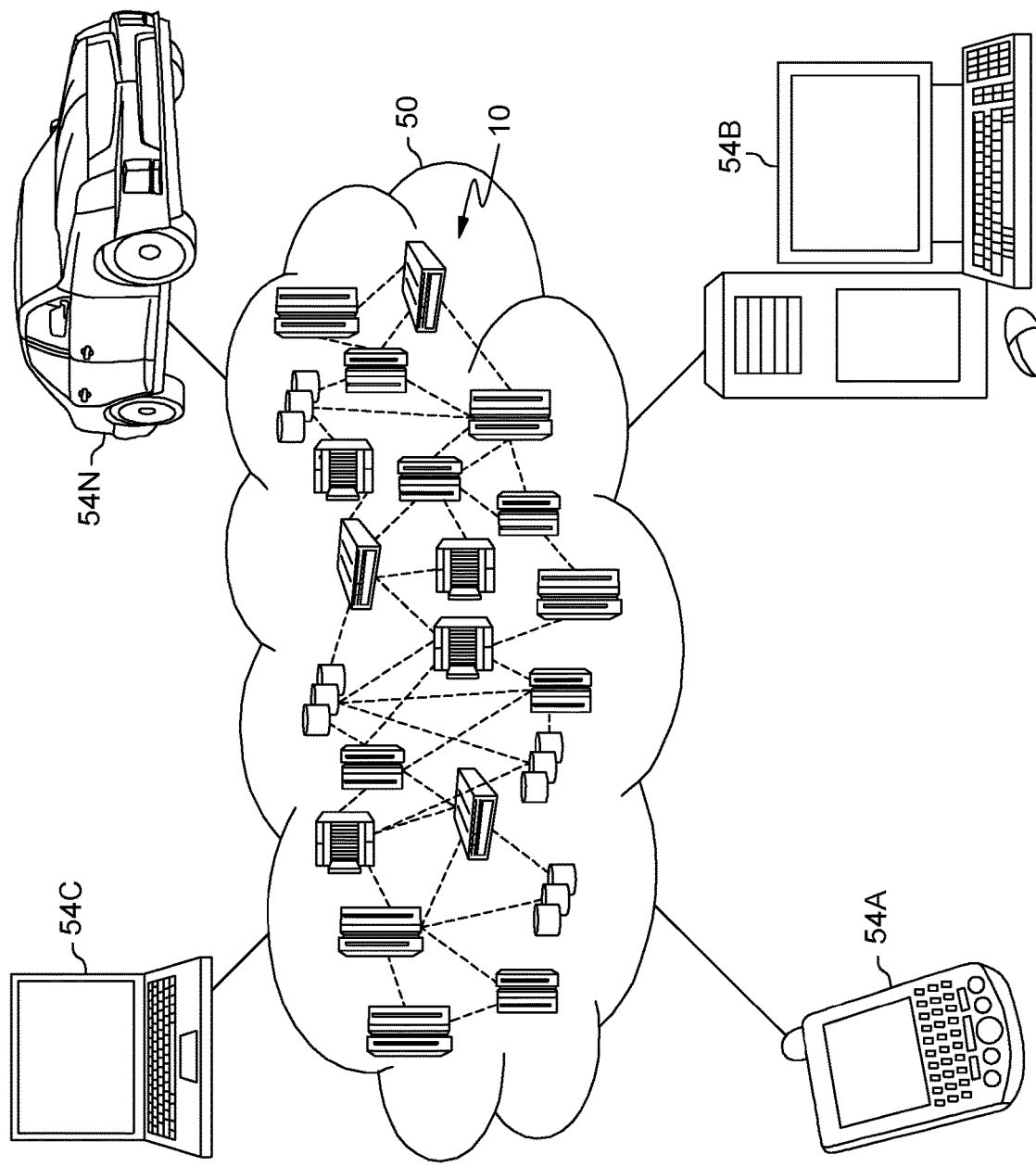
FIG. 8 depicts a cloud computing environment according to one embodiment.
Figure 9:
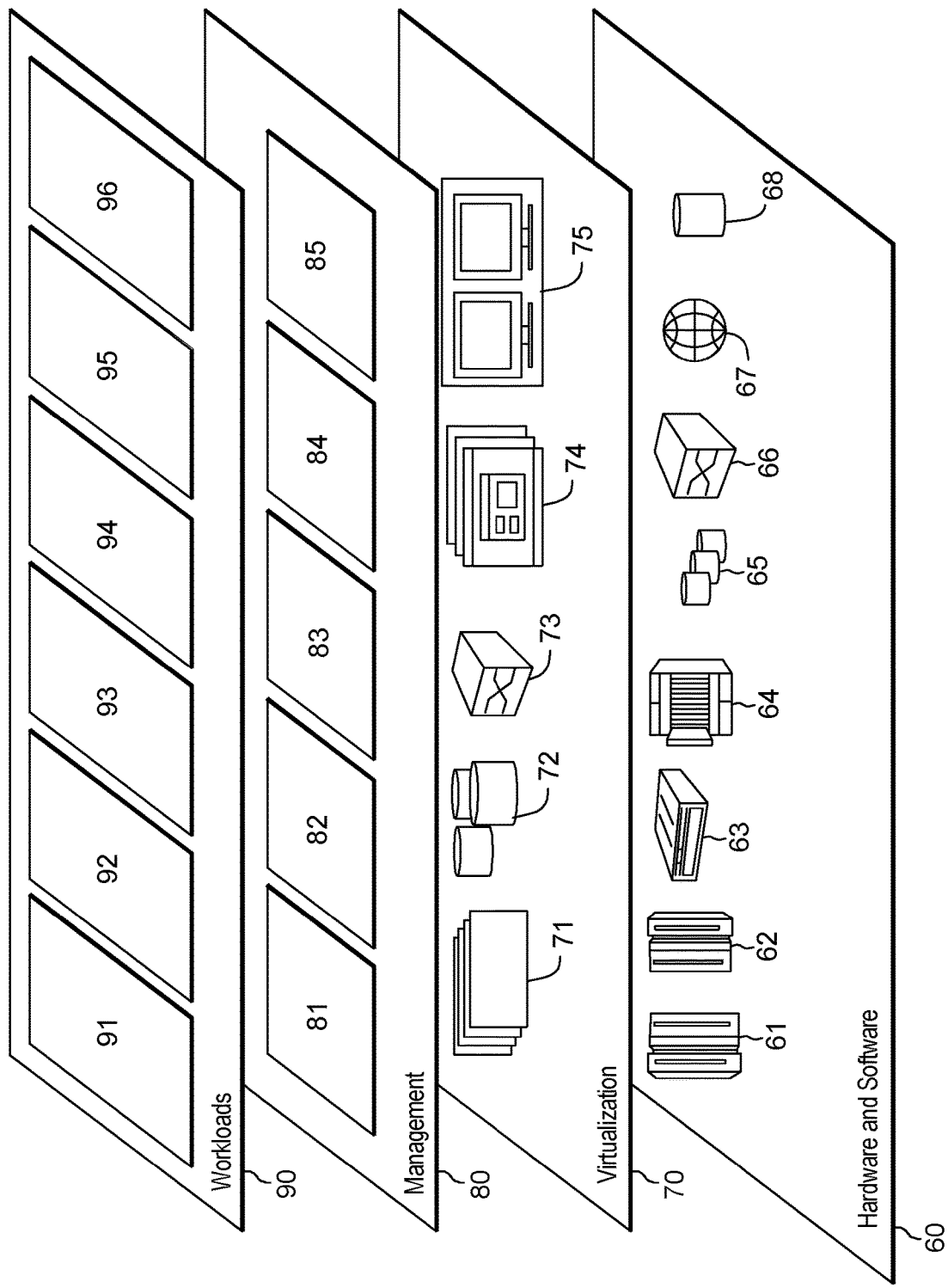
FIG. 9 depicts abstraction model layers according to one embodiment.

FIGS. 7-9 depict various aspects of computing, including a computer system and cloud computing, in accordance with one or more aspects set forth herein.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 7, a schematic of an example of a computing node is shown. Computing node 10 is only one example of a computing node suitable for use as a cloud computing node and is not intended to suggest any limitation as to the scope of use or functionality of embodiments of the invention described herein. Regardless, computing node 10 is capable of being implemented and/or performing any of the functionality set forth hereinabove. Computing node 10 can be implemented as a cloud computing node in a cloud computing environment, or can be implemented as a computing node in a computing environment other than a cloud computing environment.

In computing node 10 there is a computer system 12, which is operational with numerous other general purpose or special purpose computing system environments or configurations. Examples of well-known computing systems, environments, and/or configurations that may be suitable for use with computer system 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system 12 may be described in the general context of computer system-executable instructions, such as program processes, being executed by a computer system. Generally, program processes may include routines, programs, objects, components, logic, data structures, and so on that perform particular tasks or implement particular abstract data types. Computer system 12 may be practiced in distributed cloud computing environments where tasks are performed by remote processing devices that are linked through a communications network. In a distributed cloud computing environment, program processes may be located in both local and remote computer system storage media including memory storage devices.

As shown in FIG. 7, computer system 12 in computing node 10 is shown in the form of a computing device. The components of computer system 12 may include, but are not limited to, one or more processor 16, a system memory 28, and a bus 18 that couples various system components including system memory 28 to processor 16. In one embodiment, computing node 10 is a computing node of a non-cloud computing environment. In one embodiment, computing node 10 is a computing node of a cloud computing environment as set forth herein in connection with FIGS. 8-9.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 12 typically includes a variety of computer system readable media. Such media may be any available media that is accessible by computer system 12, and it includes both volatile and non-volatile media, removable and non-removable media.

System memory 28 can include computer system readable media in the form of volatile memory, such as random access memory (RAM) 30 and/or cache memory 32. Computer system 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program processes that are configured to carry out the functions of embodiments of the invention.

One or more program 40, having a set (at least one) of program processes 42, may be stored in memory 28 by way of example, and not limitation, as well as an operating system, one or more application programs, other program processes, and program data. One or more program 40 including program processes 42 can generally carry out the functions set forth herein. In one embodiment, manager system 110 can include one or more computing node 10 and can include one or more program 40 for performing functions described with reference to manager system 110 as set forth in the flowchart of FIG. 4. In one embodiment, respective smartwatches 120A-120Z can include one or more computing node 10 and can include one or more program 40 for performing functions described with reference to smartwatches 120A-120Z as set forth in the flowchart of FIG. 4. In one embodiment, respective UE devices 130A-130Z can include one or more computing node 10 and can include one or more program 40 for performing functions described with reference to UE devices 130A-130Z as set forth in the flowchart of FIG. 4. In one embodiment, social media system 140 can include one or more computing node 10 and can include one or more program 40 for performing functions described with reference to social media system 140 as set forth in the flowchart of FIG. 4. In one embodiment, the computing node based systems and devices depicted in FIG. 1 can include one or more program for performing function described with reference to such computing node based systems and devices.

Computer system 12 may also communicate with one or more external devices 14 such as a keyboard, a pointing device, a display 24, etc.; one or more devices that enable a user to interact with computer system 12; and/or any devices (e.g., network card, modem, etc.) that enable computer system 12 to communicate with one or more other computing devices. Such communication can occur via Input/Output (I/O) interfaces 22. Still yet, computer system 12 can communicate with one or more networks such as a local area network (LAN), a general wide area network (WAN), and/or a public network (e.g., the Internet) via network adapter 20. As depicted, network adapter 20 communicates with the other components of computer system 12 via bus 18. It should be understood that although not shown, other hardware and/or software components could be used in conjunction with computer system 12. Examples, include, but are not limited to: microcode, device drivers, redundant processing units, external disk drive arrays, RAID systems, tape drives, and data archival storage systems, etc. In addition to or in place of having external devices 14 and display 24, which can be configured to provide user interface functionality, computing node 10 in one embodiment can include display 25 connected to bus 18. In one embodiment, display 25 can be configured as a touch display screen and can be configured to provide user interface functionality, e.g. can facilitate virtual keyboard functionality and input of total data. Computer system 12 in one embodiment can also include one or more sensor device 27 connected to bus 18. One or more sensor device 27 can alternatively be connected through I/O interface(s) 22. One or more sensor device 27 can include a Global Positioning Sensor (GPS) device in one embodiment and can be configured to provide a location of computing node 10. In one embodiment, one or more sensor device 27 can alternatively or in addition include, e.g., one or more of a camera image sensor, a gyroscope, a temperature sensor, a humidity sensor, a pulse sensor, a blood pressure (bp) sensor, an ultrasound sensor or an audio input device. Computer system 12 can include one or more network adapter 20. In FIG. 8 computing node 10 is described as being implemented in a cloud computing environment and accordingly is referred to as a cloud computing node in the context of FIG. 8.

Referring now to FIG. 8, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 8 are intended to be illustrative only and that computing nodes 10 and cloud computing environment 50 can communicate with any type of computerized device over any type of network and/or network addressable connection (e.g., using a web browser).

Referring now to FIG. 9, a set of functional abstraction layers provided by cloud computing environment 50 (FIG. 8) is shown. It should be understood in advance that the components, layers, and functions shown in FIG. 9 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and processing components 96 for controlling a smartwatch as set forth herein. The processing components 96 can be implemented with use of one or more program 40 described in FIG. 7.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting. As used herein, the singular forms "a," "an," and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Forms of the term "based on" herein encompass relationships where an element is partially based on as well as relationships where an element is entirely based on. Methods, products and systems described as having a certain number of elements can be practiced with less than or greater than the certain number of elements. Furthermore, a device or structure that is configured in a certain way is configured in at least that way, but may also be configured in ways that are not listed.

It is contemplated that numerical values, as well as other values that are recited herein are modified by the term "about", whether expressly stated or inherently derived by the discussion of the present disclosure. As used herein, the term "about" defines the numerical boundaries of the modified values so as to include, but not be limited to, tolerances and values up to, and including the numerical value so modified. That is, numerical values can include the actual value that is expressly stated, as well as other values that are, or can be, the decimal, fractional, or other multiple of the actual value indicated, and/or described in the disclosure.

The corresponding structures, materials, acts, and equivalents of all means or step plus function elements in the claims below, if any, are intended to include any structure, material, or act for performing the function in combination with other claimed elements as specifically claimed. The description set forth herein has been presented for purposes of illustration and description, but is not intended to be exhaustive or limited to the form disclosed. Many modifications and variations will be apparent to those of ordinary skill in the art without departing from the scope and spirit of the disclosure. The embodiment was chosen and described in order to best explain the principles of one or more aspects set forth herein and the practical application, and to enable others of ordinary skill in the art to understand one or more aspects as described herein for various embodiments with various modifications as are suited to the particular use contemplated.

What is claimed is:

1. A computer implemented method comprising:
    obtaining data source data from one or more data source;
    processing data of the data source data, wherein the processing data of the data source data includes processing physiological data of a user wearing a smartwatch;
    controlling the smartwatch in dependence on the processing data, wherein the controlling the smartwatch adjusts a flow of air to a smartwatch supporting wrist of the user wearing the smartwatch.

2. The computer implemented method of claim 1, wherein the controlling the smartwatch in dependence on the processing data includes adjusting a display screen of the smartwatch to adjust an exposed viewing area dimension of the display screen.

3. The computer implemented method of claim 1, wherein the controlling the smartwatch in dependence on the processing data includes adjusting a display screen of the smartwatch to adjust an exposed viewing area dimension of the display screen, wherein the method includes controlling the display screen between a first display screen configuration wherein the display screen extends between first terminal end and a second terminal end of a wristband of the smartwatch, and a second display screen configuration to define a gap between the display screen and the second terminal end of the wristband.

4. The computer implemented method of claim 1, wherein the method is further characterized by one or more of the following selected from the group consisting of (a) the controlling the smartwatch in dependence on the processing data includes controlling a wristband of the smartwatch so that at a first time period, the wristband contacts the wrist at first locations of the wrist and further so that at a second time period, the wristband contacts the wrist at second locations of the wrist, (b) the method includes using data output from an ultrasound sensor of a wristband to ascertain a location of a vein within the wrist, and wherein the controlling a smartwatch includes controlling the wristband to preferentially contact the wrist at locations aligned with the vein for improved ultrasound imaging of the vein, (c) the controlling the smartwatch in dependence on the processing data includes adjusting a state of one more microbump disposed on a wrist facing interior surface of a wristband of the smartwatch, (d) the controlling the smartwatch in dependence on the processing data includes adjusting a display screen of the smartwatch to adjust an exposed viewing area dimension of the display screen that is visible to the user, wherein the controlling the smartwatch in dependence on the processing data includes adjusting a state of one more wrist contactable microbump disposed on an interior wrist facing surface of a wristband of the smartwatch, (e) wherein the processing includes querying a predictive model that has been trained with use of historical parameter values associated to the user, the querying returning a prediction as to a perspiration level at the supporting wrist of a user wearing the smartwatch, wherein the controlling the smartwatch in dependence on the processing data includes, in dependence on the prediction, controlling an activation state of a wrist contactable microbump formed on a wristband of the smartwatch, and (f) the processing includes querying a predictive model that has been trained with use of historical parameter values associated to the user, the querying returning a prediction as to a temperature at the supporting wrist of a user wearing the smartwatch, wherein the controlling the smartwatch in dependence on the processing data includes, in dependence on the prediction, controlling an activation state of a wrist contactable microbump formed on a wristband of the smartwatch.

5. The computer implemented method of claim 1, wherein the controlling a smartwatch in dependence on the processing data includes adjusting a display screen of the smartwatch between a first display screen configuration in which an imaginary vertical plane extending lengthwise with an arm of the user perpendicularly through the display screen does not intersect the wrist of the user, and a second display screen configuration in which the display screen is contained within a chamber of the smartwatch and hidden from view.

6. The computer implemented method of claim 1, wherein the controlling the smartwatch in dependence on the processing data includes activating a micro blower of a wristband of the smartwatch.

7. The computer implemented method of claim 1, wherein a wristband of the smartwatch is configured to position a display screen viewing area supporting structure in a worn position so that the supporting structure defines a gap between the supporting structure and the smartwatch supporting wrist of the user.

8. The computer implemented method of claim 1, wherein the controlling the smartwatch in dependence on the processing data includes changing shape of the smartwatch.

9. The computer implemented method of claim 1, wherein the controlling the smartwatch in dependence on the processing data includes adjusting a spatial area occupied by a structural feature of the smartwatch.

10. The computer implemented method of claim 1, wherein the controlling the smartwatch in dependence on the processing data includes controlling the smartwatch so that a structural feature of the smartwatch in contact with the smartwatch supporting wrist of the user is no longer in contact with the smartwatch supporting wrist of the user.

11. The computer implemented method of claim 1, wherein the controlling the smartwatch in dependence on the processing data includes changing a location of structural feature of the smartwatch from a first location wherein the structural feature encumbers airflow to the smartwatch supporting wrist of the user.

12. The computer implemented method of claim 1, wherein the controlling the smartwatch in dependence on the processing data includes adjusting a spatial area occupied by a display screen of the smartwatch.

13. The computer implemented method of claim 1, wherein the controlling the smartwatch in dependence on the processing data includes controlling the smartwatch so that airflow to the smartwatch supporting wrist of the user encumbered by a structural feature of the smartwatch is reduced.

14. A system comprising:
  a memory;
  at least one processor in communication with the memory; and
  program instructions executable by one or more processor via the memory to perform a method comprising:
    obtaining data source data from one or more data source;
    processing data of the data source data, wherein the processing data of the data source data includes processing physiological data of a user wearing a smartwatch;
    controlling the smartwatch in dependence on the processing data, wherein the controlling the smartwatch adjusts a flow of air to a smartwatch supporting wrist of the user wearing the smartwatch.

15. The system of claim 14, wherein a wristband of the smartwatch is configured to support a display screen of the smartwatch so that a bottom elevation of the display screen is above a top elevation of the smartwatch supporting wrist.

16. A computer implemented method comprising:
  obtaining data source data from one or more data source;
  processing data of the data source data;
  controlling a smartwatch in dependence on the processing data, wherein the controlling the smartwatch adjusts a flow of air to a smartwatch supporting wrist of a user wearing the smartwatch, wherein the controlling the smartwatch in dependence on the processing data includes adjusting a spatial area occupied by a structural feature of the smartwatch.

17. The computer implemented method of claim 16, wherein the controlling the smartwatch in dependence on the processing data includes controlling the smartwatch so that structural feature of the smartwatch in contact with the smartwatch supporting wrist of the user is no longer in contact with the smartwatch supporting wrist of the user.

18. The computer implemented method of claim 16, wherein the controlling the smartwatch in dependence on the processing data includes changing a location of the structural feature of the smartwatch from a first location wherein the structural feature encumbers airflow to the smartwatch supporting wrist of the user.

19. The computer implemented method of claim 16, wherein the structural feature includes a display screen, and wherein the controlling the smartwatch in dependence on the processing data includes adjusting a spatial area occupied by the display screen of the smartwatch.

20. The computer implemented method of claim 16, wherein the controlling the smartwatch in dependence on the processing data includes controlling the smartwatch so that airflow to the smartwatch supporting wrist of the user encumbered by the structural feature of the smartwatch is reduced.

* * * * *